(12) United States Patent
He et al.

(10) Patent No.: US 12,331,217 B2
(45) Date of Patent: Jun. 17, 2025

(54) SELF-POWERED SENSORY TEXTILE DEVICE

(71) Applicant: NATIONAL UNIVERSITY OF SINGAPORE, Singapore (SG)

(72) Inventors: Tianyiyi He, Singapore (SG); Chengkuo Lee, Singapore (SG); Qiongfeng Shi, Singapore (SG); Hao Wang, Singapore (SG); Minglu Zhu, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 1056 days.

(21) Appl. No.: 17/285,963

(22) PCT Filed: Oct. 18, 2019

(86) PCT No.: PCT/SG2019/050518
§ 371 (c)(1),
(2) Date: Apr. 16, 2021

(87) PCT Pub. No.: WO2020/081013
PCT Pub. Date: Apr. 23, 2020

(65) Prior Publication Data
US 2021/0380821 A1 Dec. 9, 2021

(30) Foreign Application Priority Data
Oct. 19, 2018 (SG) .............................. 10201809281S

(51) Int. Cl.
*C09D 5/24* (2006.01)
*A41D 1/00* (2018.01)
(Continued)

(52) U.S. Cl.
CPC ............... *C09D 5/24* (2013.01); *A41D 1/002* (2013.01); *A61B 5/112* (2013.01); *A61B 5/6807* (2013.01);
(Continued)

(58) Field of Classification Search
None
See application file for complete search history.

(56) References Cited

U.S. PATENT DOCUMENTS

2014/0338458 A1  11/2014  Wang et al.
2018/0014780 A1   1/2018  Sotzing et al.

FOREIGN PATENT DOCUMENTS

| JP | 2018021766 | 2/2018 |
|---|---|---|
| WO | 2014169724 | 10/2014 |
| WO | 2015014950 | 2/2015 |

OTHER PUBLICATIONS

International Search Report and Written Opinion for PCT/SG2019/050518 dated Jan. 9, 2021.

*Primary Examiner* — Arti Singh-Pandey
(74) *Attorney, Agent, or Firm* — Barnes & Thornburg LLP

(57) ABSTRACT

Disclosed is a method for forming a sensory textile. The method includes: providing a conductive polymer, a dopant and a solvent; mixing the conductive polymer, dopant and solvent to form a mixture having a predetermined ratio of the conductive polymer and the dopant, and a predetermined concentration of the conductive polymer; contacting a fabric with the mixture to coat the fabric with the conductive polymer and dopant; and drying the coated fabric. Also disclosed is a sensory textile device that includes such a sensory textile, a conductive backing layer and a spacer layer disposed between the sensory textile and conductive backing layer.

27 Claims, 19 Drawing Sheets

(51) Int. Cl.
    *A61B 5/00*     (2006.01)
    *A61B 5/11*     (2006.01)
    *C09D 7/80*     (2018.01)
    *C09D 165/00*     (2006.01)
    *D06N 3/04*     (2006.01)
    *H01B 1/12*     (2006.01)

(52) U.S. Cl.
    CPC ............. *C09D 7/80* (2018.01); *C09D 165/00* (2013.01); *D06N 3/045* (2013.01); *H01B 1/127* (2013.01); *A61B 2562/12* (2013.01); *D06N 2203/06* (2013.01); *D06N 2211/10* (2013.01)

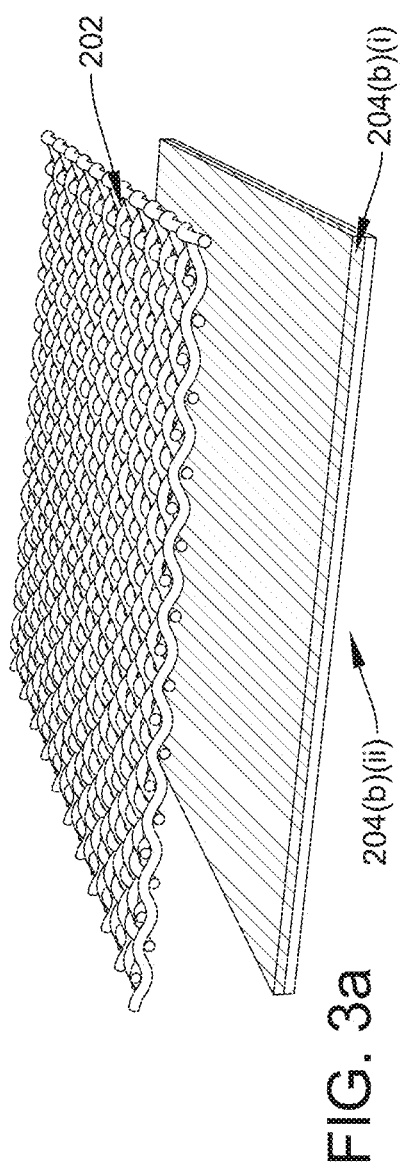
FIG. 3a
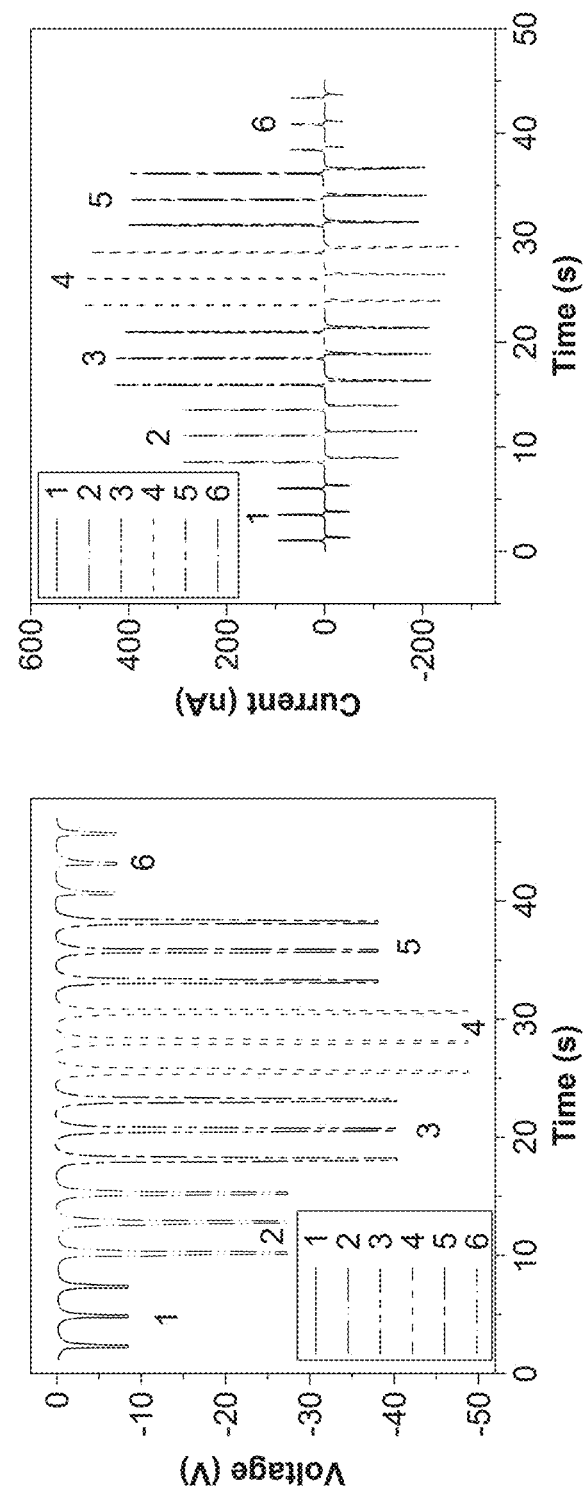
FIG. 3b
FIG. 3c

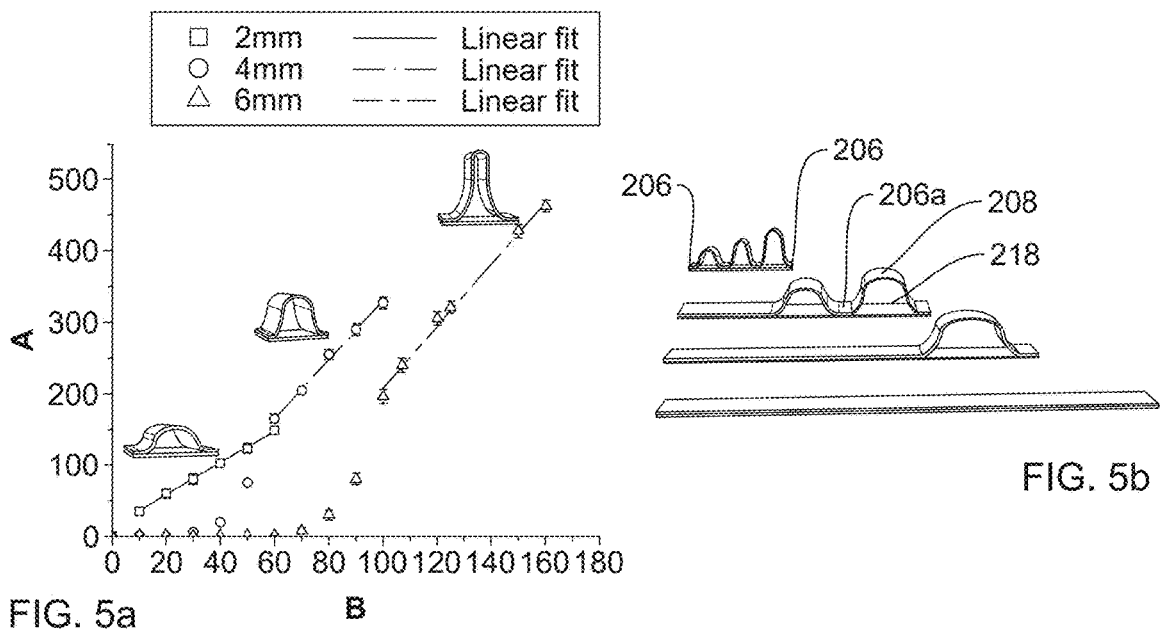
FIG. 5a
FIG. 5b
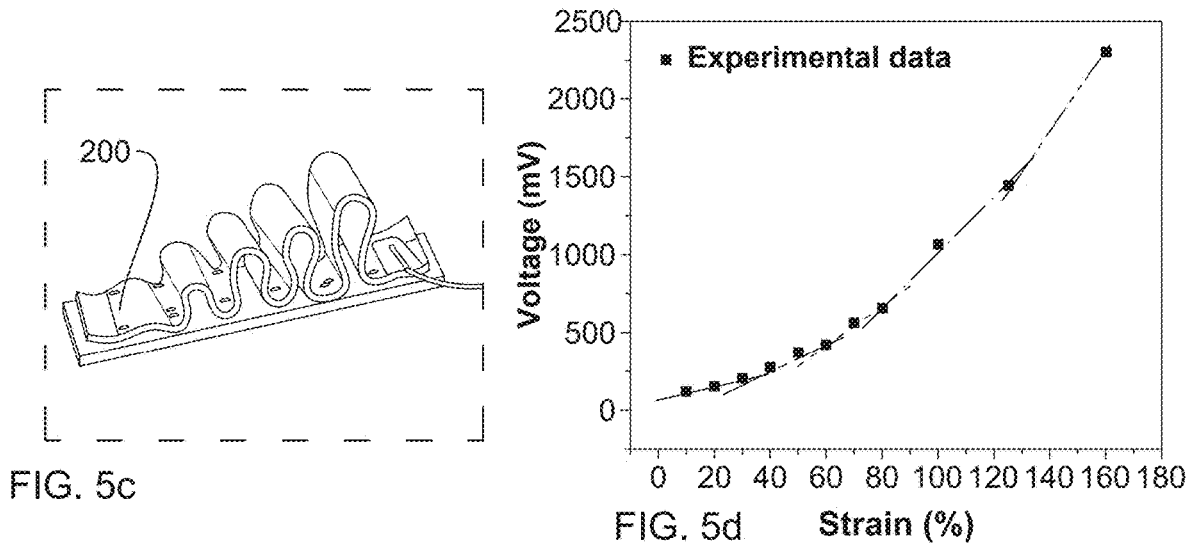
FIG. 5c
FIG. 5d
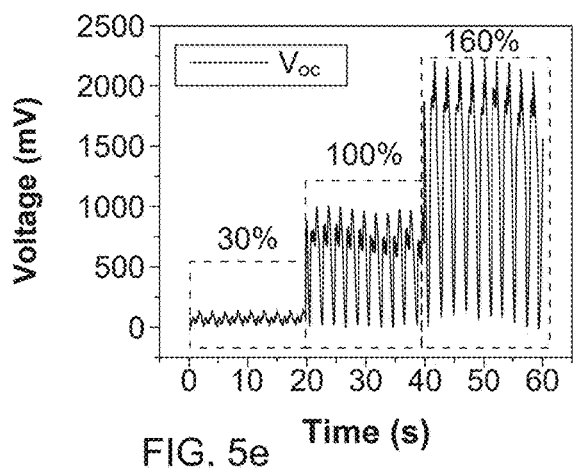
FIG. 5e

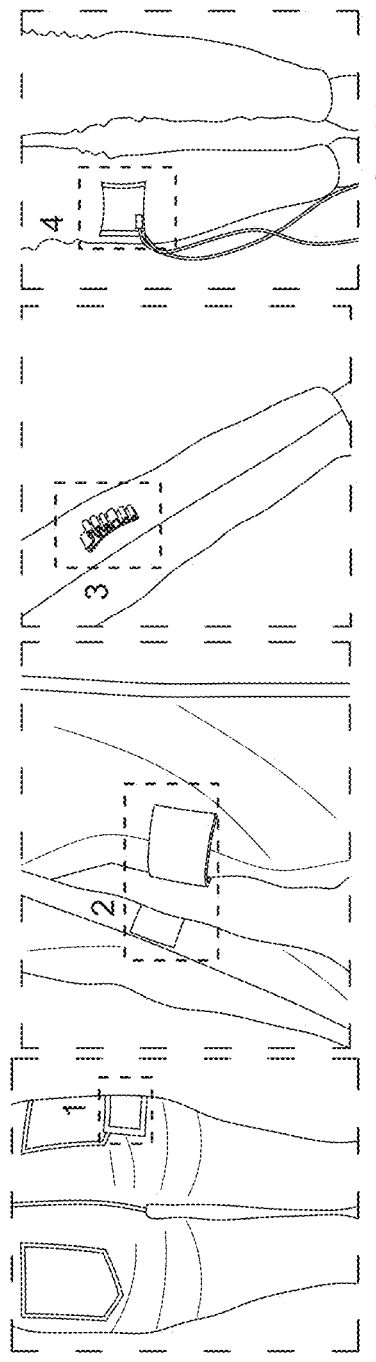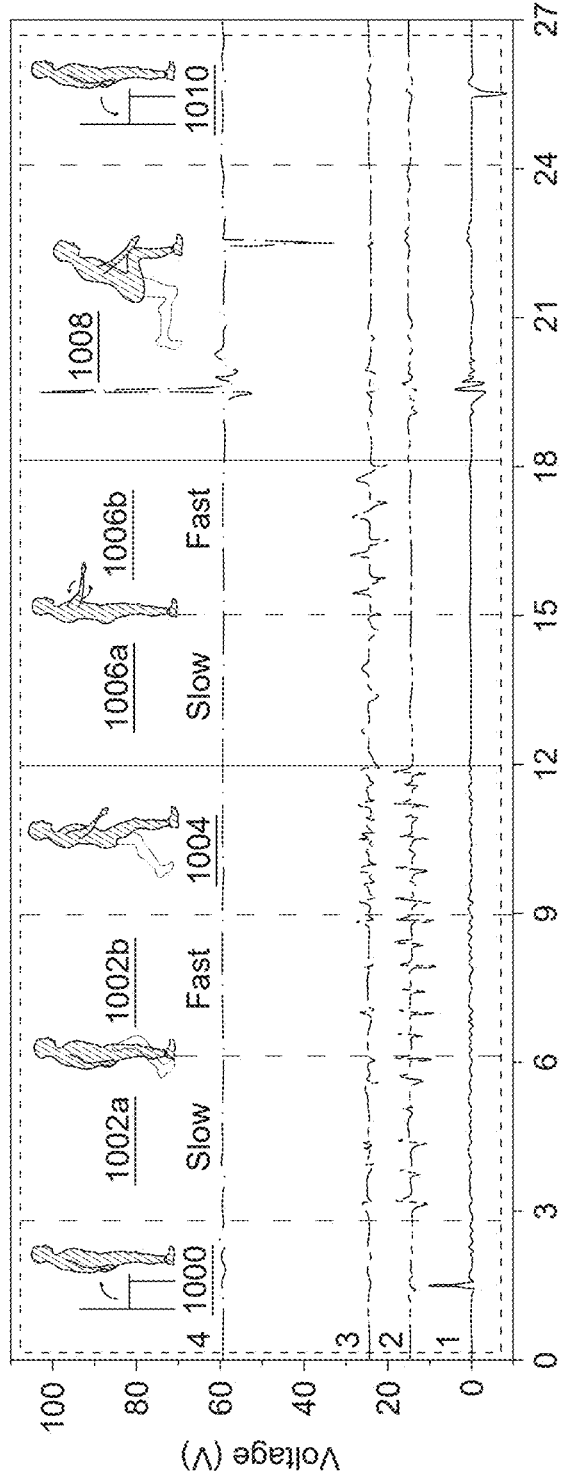

SELF-POWERED SENSORY TEXTILE DEVICE

CROSS REFERENCE TO RELATED APPLICATIONS

This application is a U.S. national stage application under 35 U.S.C. § 371 (b) of International Application No. PCT/SG2019/050518 filed Oct. 18, 2019, which claims priority to the Singapore Patent Application No. 10201809281S filed on Oct. 19, 2018, the disclosures of both of which are hereby expressly incorporated by reference in their entirety.

TECHNICAL FIELD

The present disclosure relates to a method for forming a sensory textile, and a sensory textile device. More particularly, the present disclosure relates to sensory textile devices fabricated as wearable smart textiles.

BACKGROUND

There has been increasing demand for smart garments, smart textiles or fabrics. Such smart textiles or fabrics are fabrics that incorporate electrical or electronic components that add value for the wearer.

Some smart textiles allow colour changing and lighting. There has also been demand for more useful functionality to be incorporated into such textiles.

Useful functionality can involve the provision of sensors and motion detection systems. However, many such systems require batteries that are uncomfortable when worn, or cannot provide fine resolution determination of motion.

It is desirable therefore to provide a sensory textile with enhanced, or different functionality when compared with prior art sensory textiles, or at least to provide a useful alternative.

SUMMARY OF THE PRESENT DISCLOSURE

In accordance with the present disclosure, there is provided a method for forming a sensory textile, comprising:
  providing a conductive polymer, a dopant and a solvent;
  mixing the conductive polymer, dopant and solvent to form a mixture having a predetermined ratio of the conductive polymer and the dopant, and a predetermined concentration of the conductive polymer;
  contacting a fabric with the mixture to coat the fabric with the conductive polymer and dopant; and
  drying the coated fabric.

Providing a conductive polymer may comprise providing a conductive organic polymer. The conductive polymer may be provided as a dispersion in a solution. Providing a conductive polymer may comprise providing poly(3,4-ethylenedioxythiophene):poly(styrene sulfonate) (PEDOT:PSS).

Providing a dopant may comprise providing a dopant to improve the conductivity of the conductive polymer once dried on the coated fabric. Providing a dopant may comprise providing dimethyl sulphoxide (DMSO).

Mixing the conductive polymer, dopant and solvent to form a mixture having a predetermined ratio of the conductive polymer to dopant, may comprise doping the conductive polymer with 5 wt % of the dopant.

Providing a solvent may comprise providing water. Providing water may comprise providing deionised water.

Mixing the conductive polymer, dopant and solvent to form a mixture having a predetermined concentration of the conductive polymer, may comprise mixing the conductive polymer, dopant and solvent to form a mixture having 12.5% conductive polymer.

Drying the coated fabric may comprise drying the coated fabric for at least 30 minutes at 80° C.

Also disclosed herein is a sensory textile device comprising:
  a sensory textile comprising a fabric coated in a conductive polymer and dopant at a predetermined ratio; and
  a substrate,
  wherein the sensory textile is attached to the substrate at at least two spaced apart locations and has a rest condition, in which the sensory textile is spaced from the substrate between the at least two spaced apart locations, and a generating condition, in which the sensory textile is in contact with the substrate between the at least two spaced apart locations.

The sensory textile may form an arch between the at least two spaced apart locations, and stretching the substrate brings the sensory textile into the generating condition. The sensory textile may form two or more arches, the two or more arches being attached to the substrate between respective pairs of locations of said at least two spaced apart locations. Thus, the sensory textile being spaced from the substrate between the at least two spaced apart locations includes the sensory textile being spaced from the substrate over the length of the sensory textile between the two spaced apart locations and, in embodiments such as those incorporating two or more arches, the sensory textile being spaced from the substrate at various parts of its length between the at least two spaced apart locations. In alternative embodiments, arches of a continuous piece of sensory textile may be considered to be spaced from the substrate, with two of the at least two spaced apart locations being between the arch and a neighbouring arch and/or between the arch and the end of the continuous piece.

The sensory textile may comprise at least two sensory textile portions attached to the substrate in a non-contacting arrangement.

The sensory textile device may be configured to be worn on a finger, the spaced apart locations being on opposite sides of a knuckle of the finger. Where two or more arches are provided, the pairs of locations of one of said two or more arches may be located on opposite sides of a knuckle of the finger and the pairs of locations of a different one of said two or more arches may be located on opposite sides of a different knuckle of the finger.

Each of said two or more arches may be of a different size to at least one other of said two or more arches.

The sensory textile device may comprise a single strip of the sensory textile, and said two or more arches form a series of arches along the strip. The series of arches may be of progressively larger size.

The sensory textile of the sensory textile device may be formed by the method described above.

Further disclosed herein is a sensory textile device comprising:
  a sensory textile formed according to the method described above;
  a conductive backing layer; and
  a spacer layer disposed between the sensory textile and conductive backing layer.

The spacer layer may be polytetrafluoroethylene (PTFE). The conductive backing layer may be Aluminium.

The sensory textile may be configured to be positioned at a first location on a human body, and the spacer layer and conductive backing may be configured to be positioned at a second location on the human body that moves past the first location during a movement of the human body, thereby to activate the sensory textile device.

Further, described herein is a garment comprising a sensory textile device as described above. The garment may be a sock for sensing a gait of a user.

BRIEF DESCRIPTION OF THE DRAWINGS

Some embodiments of sensory textiles and methods for forming sensory textiles will be now be described by way of non-limiting example only, with reference to the accompanying drawings in which:

FIG. 2, comprising

FIG. 2a—various configurations of a smart textile—e.g. poly(3,4-ethylenedioxythiophene):poly(styrene sulfonate) (PEDOT:PSS)—as applied to multiple parts of a human body;

FIG. 2b—an image of the smart textile of FIG. 2a and a scanning electron microscope (SEM) enlarged view of a portion of that image; and FIG. 2c—the mechanism by which a triboelectric nano-generator (TENG) formed using the smart textile of FIG. 2a operates;

FIG. 3, comprising FIGS. 3a to 3c, illustrates:

FIG. 3a—a schematic diagram of a smart textile formed in accordance with present teachings;

FIG. 3b—the open-circuit output voltage of the smart textile a various doping concentrations of a dopant; and FIG. 3c—the short-circuit output current of the smart textile a various doping concentrations of a dopant;

FIG. 4, comprising

FIG. 4a—voltage output for repetitive clapping or hand tapping over time;

FIG. 4b—output power of the repetitive clapping or hand tapping of FIG. 4a, versus resistance;

FIG. 4c—voltage output for repetitive stepping over time;

FIG. 4d—output power of the repetitive stepping of FIG. 4c, versus resistance;

FIG. 4e—the charging curve for various capacitors under the repetitive clapping or hand tapping of FIG. 4a; and FIG. 4f—the charging curve for various capacitors under the repetitive stepping of FIG. 4c;

FIG. 5, comprising FIGS. 5a to 5e, illustrates:

FIG. 5a—output amperage of single-arch strain sensors of various heights;

FIG. 5b—schematic diagram of multi-arch strain sensor under progressive stretching;

FIG. 5c—image of multi-arch strain sensor;

FIG. 5d—output voltage of multi-arch strain sensor of FIG. 5c; and

FIG. 5e—real-time output of multi-arch strain sensor of FIG. 5c under various strains;

FIG. 6, comprising

FIG. 6a—image of a coated textile strip; and

FIG. 6b—change in resistance over varying amounts of strain;

FIG. 7, comprising

FIG. 7a—image of a two-arch sensor for measuring finger movements, mounted to a hand;

FIG. 7b—image of the sensor and hand of FIG. 7a, with the hand bent to activate a first of the arches of the two-arch sensor;

FIG. 7c—image of the sensor and hand of FIG. 7a, with the hand bent to activate a second of the arches of the two-arch sensor;

FIG. 7e—design incorporating two separate sensors located at respective finger joints (e.g. knuckles);

FIG. 7i—design incorporating a two-arch sensor, each arch being located at a respective finger joint;

FIGS. 7f and 7j—voltage outputs at a first of the two sensors of the device of FIG. 7e, and a first of the two arches of the device of FIG. 7i, respectively, at various angles of bending of a first finger joint;

FIGS. 7g and 7k—voltage outputs at a second of the two sensors of the device of FIG. 7e, and a second of the two arches of the device of FIG. 7i, respectively, at various angles of bending of a second finger joint; and FIGS. 7h and 7l—voltage outputs at both the first and second of the two sensors of the device of FIG. 7e, and both the first and second of the two arches of the device of FIG. 7i, respectively, at various angles of bending of the first and/or second finger joints;

FIG. 8, comprising

FIG. 8a—image of two, two-arch sensors mounted to a human hand;

FIG. 8b—illustrated hand forming letters A, B, C and D in American Sign Language; and FIGS. 8c to 8f—the voltage outputs of the four arches of the two, two-arch sensors of FIG. 8a for American Sign Language letters A, B, C and D respectively;

FIG. 9, comprising

FIG. 9a—images of hand gestures performed with four sensors, one mounted to each finger;

FIG. 9b—open circuit output voltages from the sensors, for each gesture shown in FIG. 9a; and FIG. 9c—a robotic hand being controlled using the open circuit voltages of FIG. 9b;

FIG. 10, comprising FIGS. 10a to 10e, illustrates:

FIGS. 10a to 10d—images of sensors attached to clothing at various locations on the human body; and FIG. 10e—open circuit voltage readings from the sensors for a variety of activities;

FIG. 11, comprising

FIG. 11a—schematic diagram of a test setup of a polyethylenimine (PEI) coated carbon dioxide ($CO_2$) sensing textile; and FIG. 11b—charge responses of the sensing textile of FIG. 11a versus varying $CO_2$ concentration;

FIG. 12, comprising

FIG. 12a—image of PEDOT:PSS coated socks (background) and original, uncoated socks (foreground);

FIG. 12b—image of piezoelectric (PZT) sensor arrays on a polydimethylsiloxane (PDMS) substrate before being embedded into the socks of FIG. 12a; and FIG. 12c—a PZT sensor unit;

FIG. 13, comprising

FIGS. 13a and 13b—output voltage and current, respectively, of PEDOT:PSS coated socks and non-coated socks; and FIGS. 13c and 13d—power curve of smart socks within shoes and without shoes, respectively, under walking and jumping conditions;

FIG. 14, comprising

FIG. 14a—gait monitoring using multiple electrodes, for toe and heel contact;

FIG. 14b—output voltage versus force calibration for piezoelectric force sensors; and FIG. 14c—output signals from ball and heel of foot during walking, and comparison against theoretical foot pressure mapping.

DETAILED DESCRIPTION OF PREFERRED EMBODIMENTS

Proposed herein is a smart textile for diversified wearable applications. Embodiments will generally be described with reference to a PEDOT:PSS coated smart textile for the applications of energy harvesting, physiological and chemical sensing, as well as controlling purposes. The smart textile is fabricated with a facile and low-cost process. The smart textile has triboelectric properties such that it experiences contact electrification. The triboelectric properties of the textile are optimized or improved as described herein, and its energy harvesting properties are investigated.

Smart textiles developed in accordance with present teachings have successfully achieved a maximum output power of 3.2 mW with foot stepping (e.g. walking) at a load of 10MΩ.

Sensory textile devices disclosed herein may comprise a single arch strain sensor or varying-height multi-arch strain sensor using the smart textile of present teachings, with a wide sensing range from 10% to 160%. Additionally, a resistance variation-based strain sensor is also characterized.

Figure 8A:
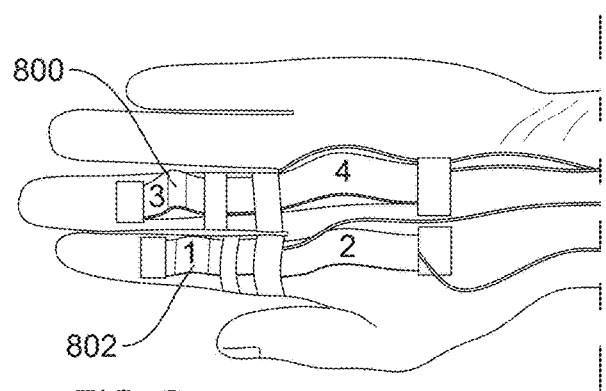
FIGS. 8a to 8f, illustrates.
Figure 8B:
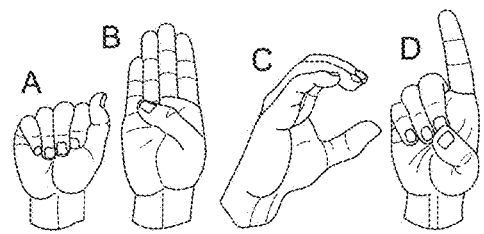
Figure 8C:
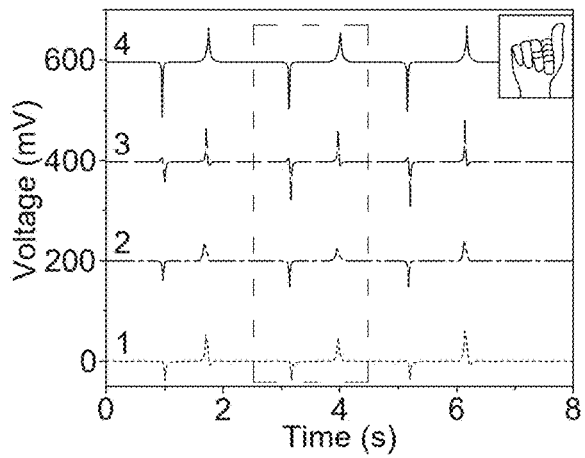
Figure 8D:
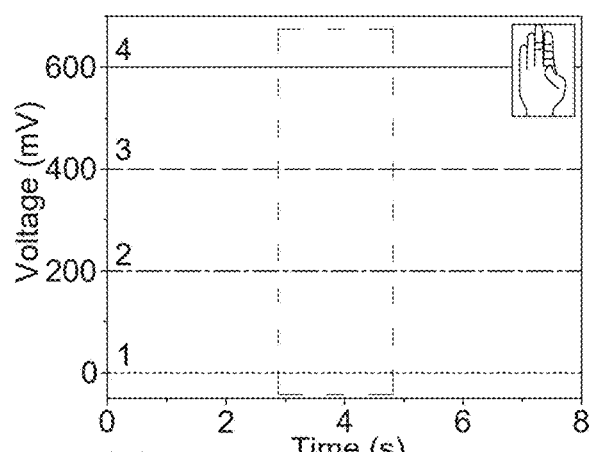
Figure 8E:
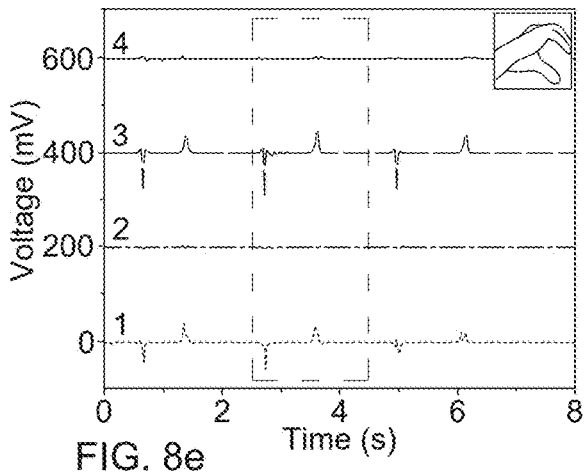
Figure 8F:
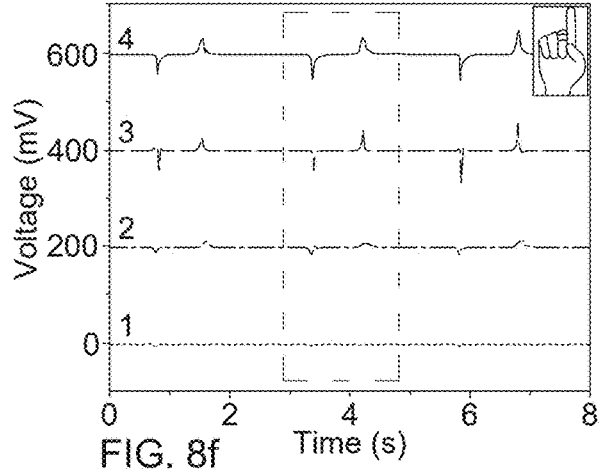
Figure 9A:
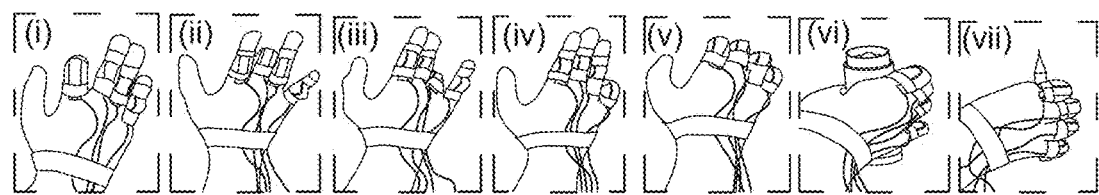
FIGS. 9a to 9c, illustrates.
Figure 9B:
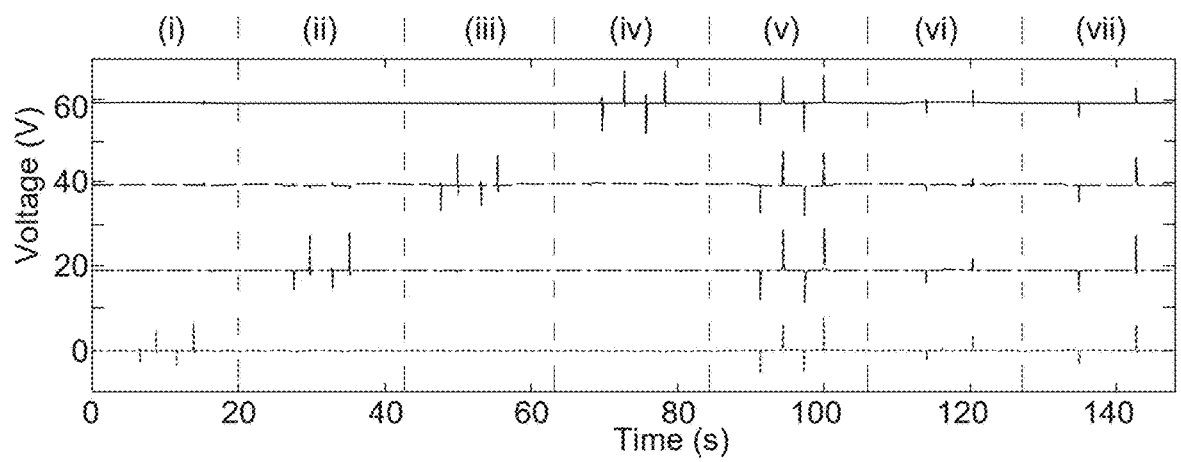
Figure 9C:
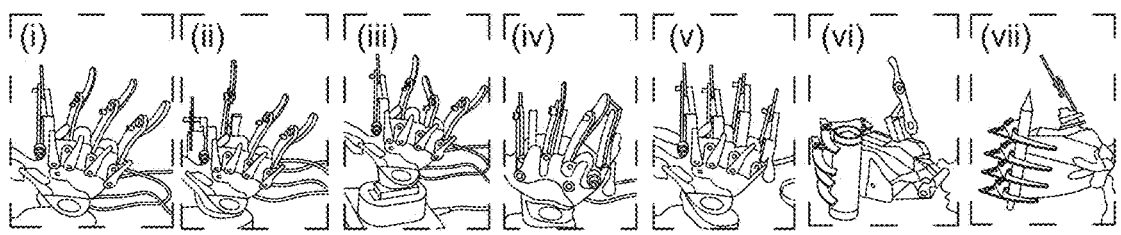

With reference to FIGS. 7 to 9, by leveraging arch-shaped strain sensors as disclosed herein positioned on human fingers, finger motions can be monitored and differentiated between. This functionality can be useful in healthcare applications such as patient monitoring, and in robot control.

In some embodiments, four self-powered sensors based on the smart textile are fabricated and attached on different parts of human body for activity monitoring. Together, the sensors are able to detect the actions of standing up, walking, running, arm bending, sudden falling, and sitting. Additional sensors will be able to identify additional movements, or provide be able to monitor the extent of those movement with greater resolution—e.g. finer differences between angles of an arm during bending In addition, the smart textile disclosed herein can also be used for CO2 sensing with a PEI coating, and a wearable arch shaped $CO_2$ sensor based on the smart textile may be fabricated.

For real cloth applications—e.g. in the fabrication of smart garments, wearable smart sensory devices and the like—smart socks are fabricated to enable energy harvesting (e.g. in triboelectric nanogenerators (TENG)) for human motion such as walking and jumping. The sensory textiles and sensory textile devices disclosed herein may be incorporated into other garments, such as shirts, pants, shoes and elsewhere.

With the aid of multiple electrodes, various human motion states and gaits can be detected. For more quantitative sensing, thin piezoelectric (PZT) sensors can also be embedded into socks to perform force analysis on the foot. Smart socks are then able to monitor or infer the level or perspiration of a human by taking the PZT sensor as a reference part. The PZT sensor output may be used as a baseline for inferring a difference in function of a triboelectric sensor in the same garment, or placed near or on the PZT sensor, and thereby infer the extent to which the triboelectric sensor has been effected by perspiration.

Poly(3,4-ethylenedioxythiophene):poly(styrene sulfonate) (PEDOT:PSS) has been found to be a successful conducting polymer for practical applications—e.g. in garments and wearable smart devices—having good film forming ability, high electrical conductivity, intrinsically high work function and good physical and chemical stability in air.

Although PEDOT:PSS is a flexible polymer, it is not stretchable intrinsically. With the aid of chemical enhancers which change morphology and act as conductivity-enhancing dopants, PEDOT:PSS can be stretched up to 100% with a minor decrease in conductivity.

Through incorporation with stretchable textile substrates, the PEDOT:PSS textile composited film is also able to be stretched to 80% while maintaining its electrical conductivity.

In accordance with the present disclosure, a facile and low-cost approach to fabricate a smart textile, interchangeably referred to as a sensory textile, is disclosed. The smart textile may be used for both energy harvesting and sensing.

Figure 2A:
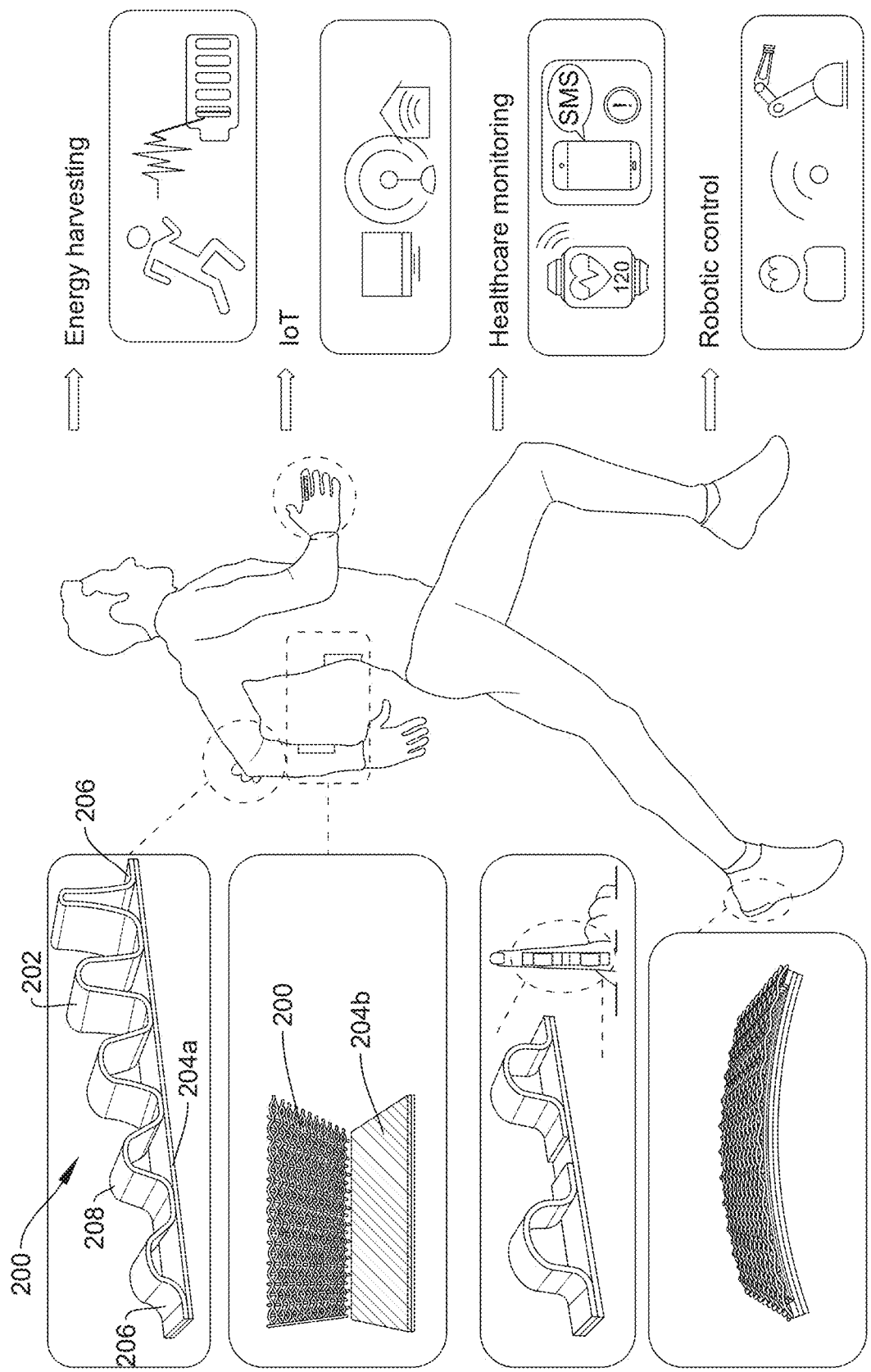
FIGS. 2a to 2c, illustrates.

A fabric used as the substrate for the sensory textile may be, for example, a 100% cotton textile owing to its advantages of being soft, light, tough, breathable, and easily available in the market. The smart textile can be easily fabricated through coating the cotton textile with PEDOT:PSS solution as shown in FIG. 2b, with FIG. 2 shows (a) applications of PEDOT:PSS coated smart textile, (b) SEM image of coated textile, and (c) working mechanism of triboelectric nanogenerator for smart textile.

Figure 1:
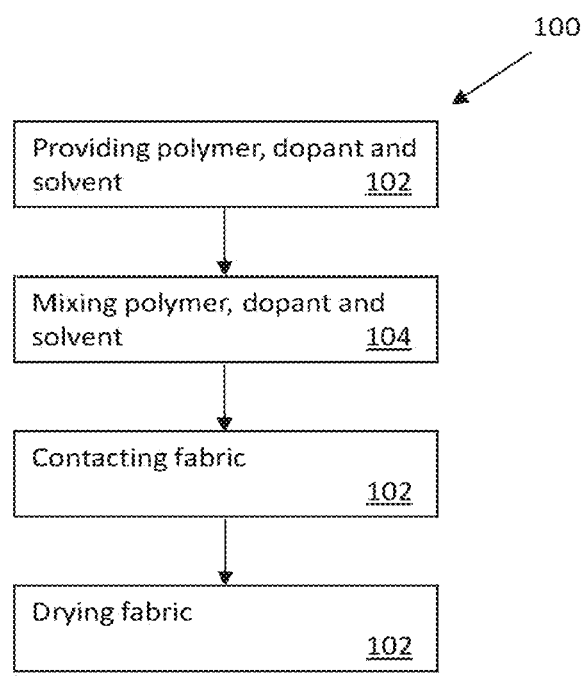
FIG. 1 illustrates a method for forming a sensory textile.
Figure 2B:
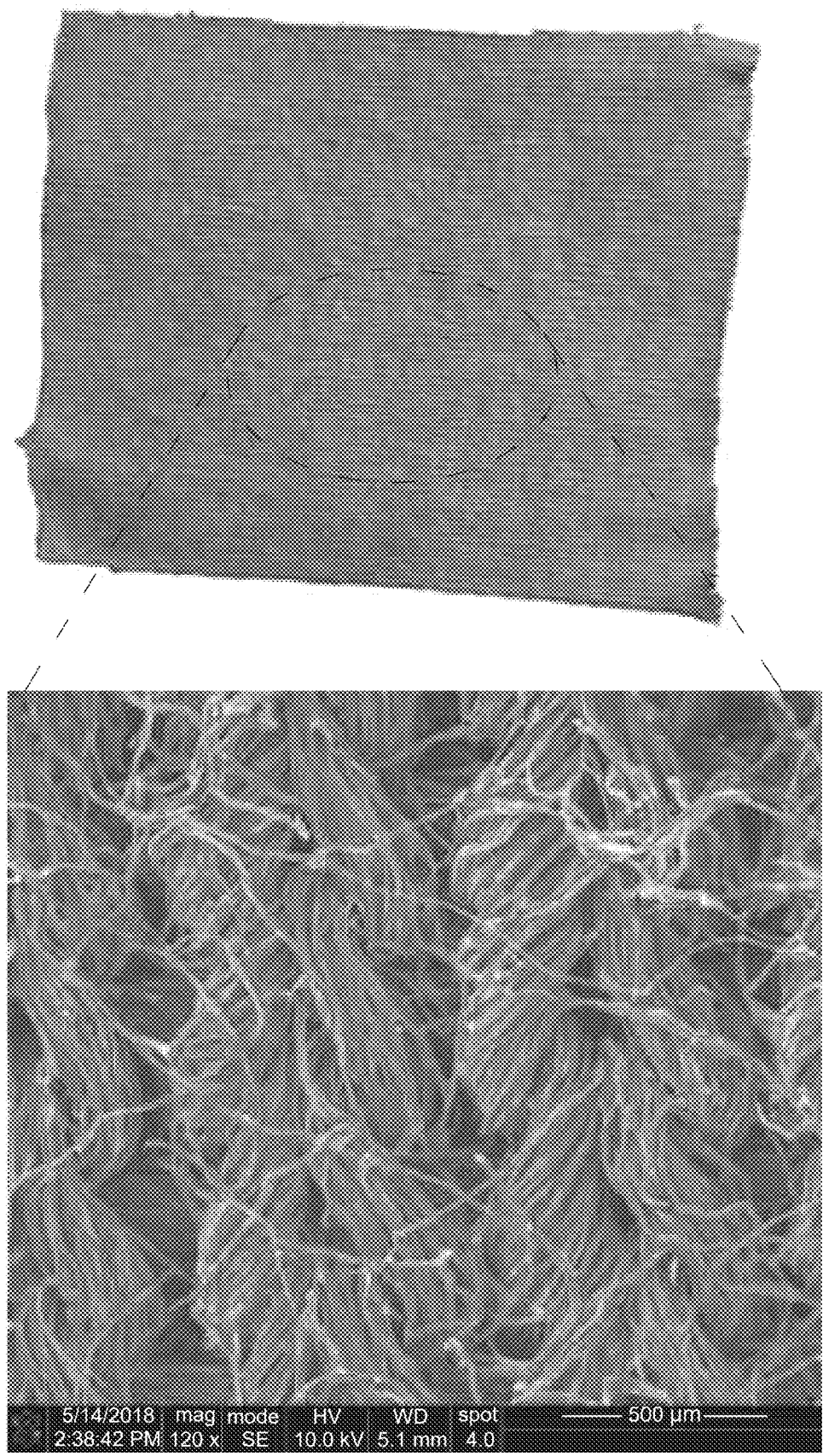
Figure 2C:
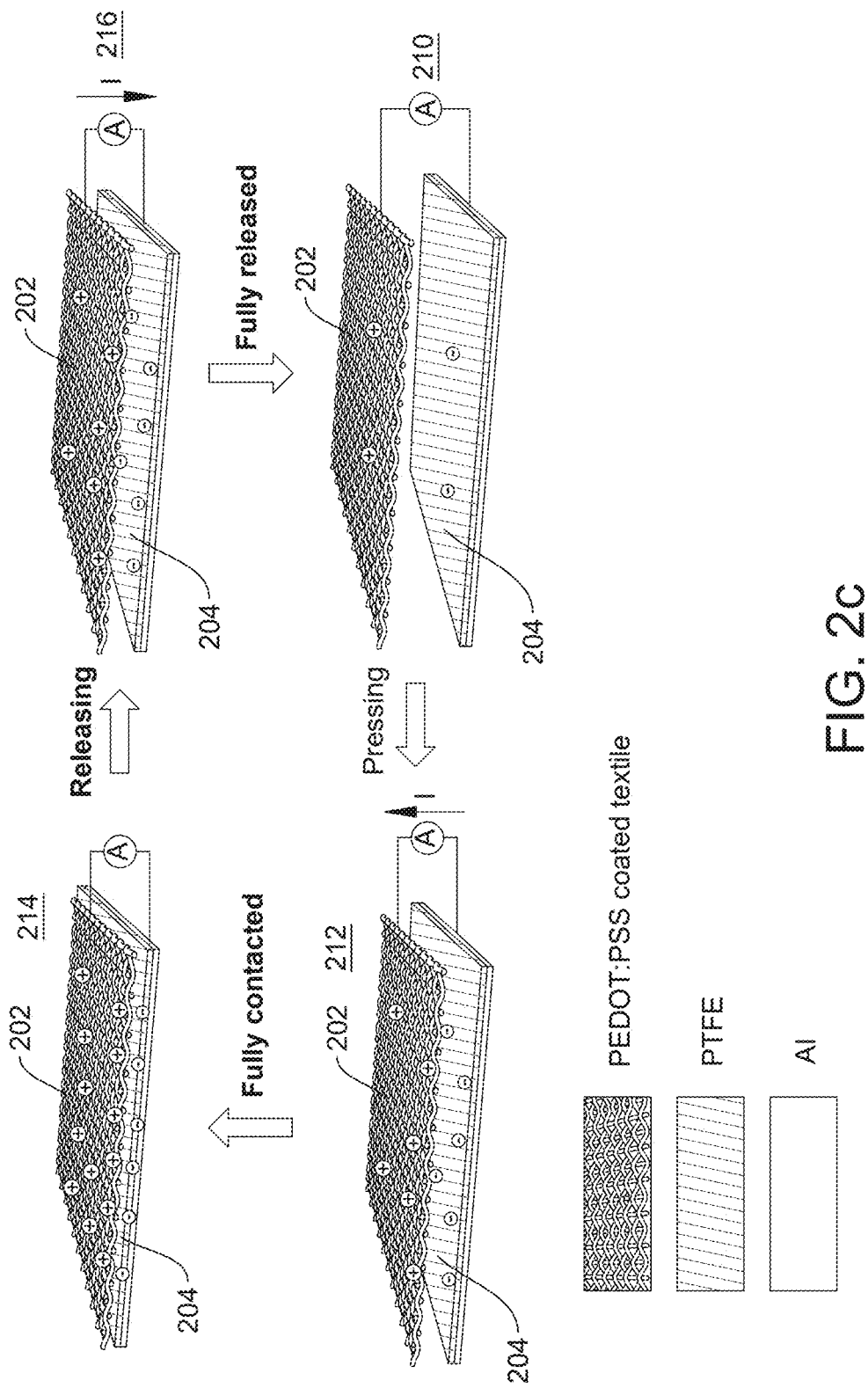

A method 100 for forming a sensory textile is set out in the flow diagram of FIG. 1, and is reflected in the textile shown in FIG. 2b. The method 100 for forming a sensory textile broadly comprises the steps of:

Step 102: providing a conductive polymer, a dopant and a solvent;

Step 104: mixing the conductive polymer, dopant and solvent;

Step 106: contacting a fabric with the mixture formed by step 104; and

Step 108: drying the coated fabric.

to form a mixture having a predetermined ratio of the conductive polymer and the dopant, and a predetermined concentration of the conductive polymer;

contacting a fabric with the mixture to coat the fabric with the conductive polymer and dopant; and drying the coated fabric.

Step 102 is self-explanatory, and example compounds for the polymer, dopant and solvent are discussed below.

Step 104 involves forming a mixture. To achieve the electromechanical properties of the sensory textile, particularly triboelectric properties in some embodiments, the dopant and conductive polymer are mixed at a predetermined ratio, and with a predetermined concentration of the conductive polymer.

Step 106 involves coating the fabric with the conductive polymer and dopant, by contacting the fabric with the mixture formed by step 104.

Step 108 may involve drying at a particular temperature, or under specific conditions to yield the sensory textiles described herein. Or may involve air drying. This step is discussed below in more detail.

The conductive polymer may be provided in step 102 as a dispersion in a solution. Thus, the ratio may be the ratio of dopant to conductive polymer solution, and the concentration may be a concentration of the conductive polymer solution. Moreover, the conductive polymer may be a conductive organic polymer.

Before the coating process, and before, after or as the conductive polymer solution is mixed with the solvent, as-purchased conductive polymer solution (e.g. PEDOT: PSS solution or other solution that is stable in air) may be doped with a dopant per step 104. The dopant may improve the conductivity of the conductive polymer solution once dried on the coated fabric (i.e. the conductive polymer derived from the solution), per Step 108.

Mixing the dopant with the conductive polymer solution per Step 104 may involve mixing demethyl sulphoxide (DMSO) with the conductive polymer solution. The mixture may be 5 wt % of dopant (e.g. (DMSO)) solution to improve its conductivity. The doped PEDOT:PSS solution, or doped conductive polymer, may then be diluted by different ratios of the solvent to determine optimum dilution—for example, 12.5% conductive polymer. After dilution, a fabric—e.g. pure cotton textile—is contacted with the mixture—per Step 106—by being immersed in the mixture or coating solution for a predetermined period of time—e.g. 10 minutes—for full absorption. The solvent may be, for example, water (e.g. deionised (DI) water).

The wet or coated textile may then be dried—e.g. by placing the coated textile into an oven and baked for at least 30 minutes at 80° C., or a temperature at which the dopant is not removed—until fully dried, per Step 108. It will be appreciated that various drying conditions may suit different types of solvent, conductive polymer or dopant, and the drying Step 108 may be adjusted accordingly, without departing from the scope of the present disclosure.

Thus, with reference to FIG. 2, a sensory textile device 200 can be produced comprising a fabric coated in a conductive polymer and dopant 202. The sensory textile device 200 also comprises a substrate which may be silicon rubber as indicated by reference numeral 204a or, as indicated by reference numeral 204b, PTFE with an Aluminium backing layer. In this sense the sensory textile comprises a conductive backing layer, and a spacer layer disposed between the sensory textile and conductive backing layer. The spacer layer may be the polytetrafluoroethylene (PTFE) layer. The conductive backing layer may be the Aluminium backing layer.

The sensory textile is attached to the substrate at at least two spaced apart locations 206. Thus, differences in length of the substrate and textile between the spaced apart locations will cause one of the substrate and textile to bulge or form a loop or arch, one of which is identified by numeral 208. The textile 200 has a rest condition, in which the sensory textile is spaced from the substrate between the at least two spaced apart locations. The textile also has a generating (i.e. operative) condition, in which the sensory textile is in contact with the substrate between the at least two spaced apart locations. Where the sensory textile forms an arch between the at least two spaced apart locations, stretching the substrate brings the sensory textile into the generating condition.

In use, the device 200 starts in an 'at rest' condition in which the sensory textile 202 is spaced—along its length or at various locations along its length—from the substrate 204, as indicated by numeral 210. Pressing the sensory textile 202 against the substrate 204, as shown by numeral 212, which may involve stretching the substrate 204, causes the textile 202 and substrate 204 to approach and, per numeral 214, touch. That contact results in charge generation. On release of the sensory textile 202, e.g. by relaxing the substrate 204, the charge flows from the textile 202 to the substrate 204 as indicated by numeral 216.

The charge thus generated may be used in energy harvesting applications, to power sensors to facilitate communication of information in an Internet of Things (IoT) application, in healthcare monitoring again using sensory systems powered by the harvested energy, or in robotic control to detect, for example, an extent of movement of a robotic arm or rotation of a joint.

FIG. 3 a sensory textile 202 formed in accordance with method 100 in a smart textile device that also includes a substrate that is spaced from the sensory textile 202 when in at 'at rest' condition as shown in FIG. 3a—i.e. the substrate has not be stretched so that the sensory textile 202 has not been brought towards, or against, the substrate 204. In this embodiment, the substrate comprises a polymer layer 204b(i), presently PTFE, and an Al backing layer 204b(ii).

FIGS. 3b and 3c show electrical properties of diluted solutions of 6 different doped PEDOT:PSS concentrations: (1) 100%+double coating, (2)100%, (3)25%, (4)12.5%, (5)6%, (6)3%. The characterization of the open-circuit voltage (VOC) is shown in FIG. 3b and the short-circuit current (ISC) is shown in FIG. 3c. In this case, a 12.5 wt % PEDOT:PSS solution shows the best performance of the six tested concentrations. Relevantly, FIG. 3 generally shows characterization of a PEDOT:PSS coated smart textile (i.e. functionalized fabric) under 6 different doped PEDOT:PSS concentrations: (1) 100%+double coating, (2)100%, (3)25%, (4)12.5%, (5)6%, (6)3% for which there is (a) a schematic diagram of a smart textile, (b) output voltage and (c) output current.

While the sensory textile may comprise a single arch, in cases shown in FIGS. 2, 5, 7 and 10 the sensory textile forms two or more arches 208, the two or more arches 208 being attached to the substrate 204 between respective pairs of locations 206 of said at least two spaced apart locations—the two or more locations may also include locations between adjacent regions at which the sensory textile is spaced from the substrate (i.e. arches) such as at location 206a as shown in FIG. 5. In some embodiments, the sensory textile comprises two, or at least two, sensory textile portions attached to the substrate in a non-contacting arrangement—see, for example, FIG. 7a. Some embodiments may be configured to be worn on a finger, the spaced apart locations being on opposite sides of a knuckle of the finger. This enables flexion or bending, and the degree of flexion or bending, of the knuckle to be identified. Where two or more arches are provided on a single finger, the flexion or bending at multiple knuckles may be measured.

Energy Harvesting Using the Smart Textile

As discussed above, a smart textile based triboelectric nanogenerator (TENG) is as shown in FIG. 2a. The PEDOT: PSS functionalized textile works both as a triboelectric positive layer and electrode. The Polytetrafluoroethylene (PTFE) thin film is used to generate negative charges. Thus, current can flow between the textile and PTFE thin film.

Figure 4A:
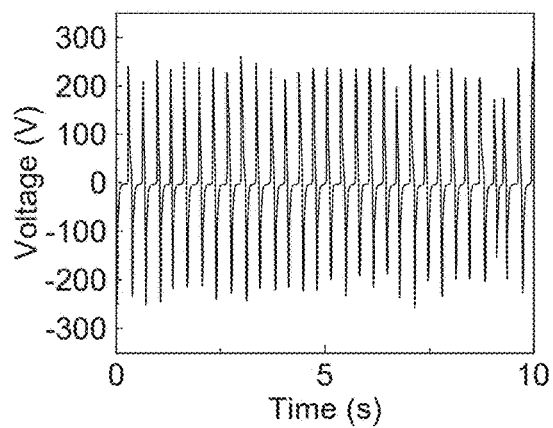
FIGS. 4a to 4f, illustrates.

The textile can be attached at various locations on the human body—e.g. on the human palm—and the PTFE thin film may be fixed on a table, both the textile and film having a consistent size—e.g. 4 cm×4 cm. A clapping or hand tapping frequency of 2 Hz or 3 Hz may then be measured. For illustration purposes, the output voltage collected from this tapping motion with a 100MΩ probe is depicted in FIG. 4a. Relevantly, FIG. 4 shows the maximum output voltage for FIG. 4(*a*) hand tapping, FIG. 4(*c*) foot stepping, and output power under different loading resistance for FIG. 4(b) hand tapping, and FIG. 4(d) foot stepping. FIG. 4 also shows the charging curve for FIG. 4(e) hand tapping, and FIG. 4(f) foot stepping.

Figure 4B:
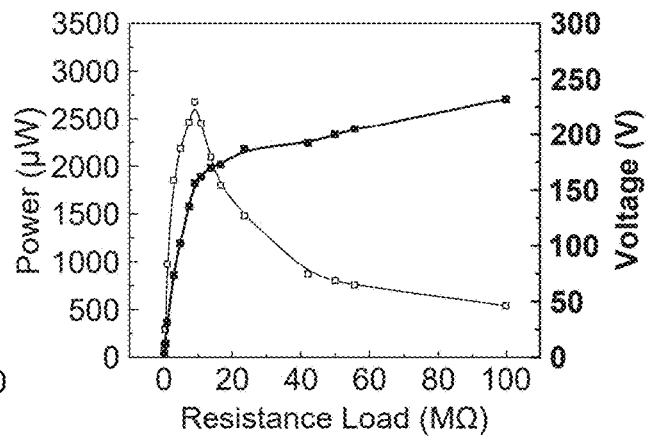
Figure 4C:
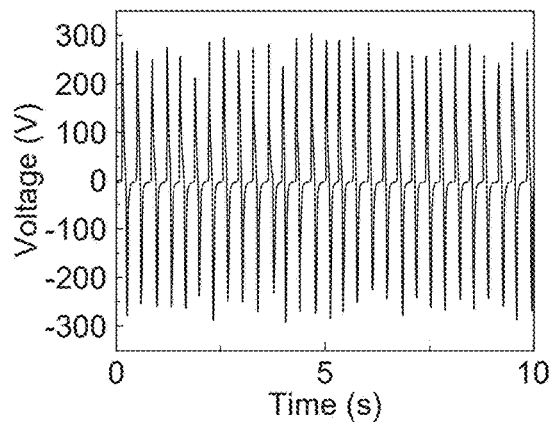
Figure 4D:
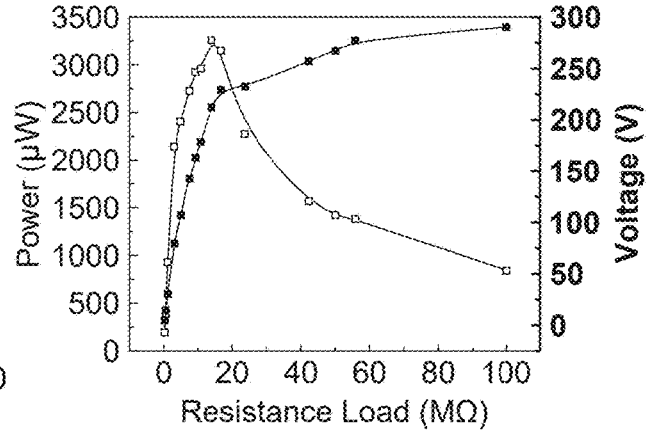
Figure 4E:
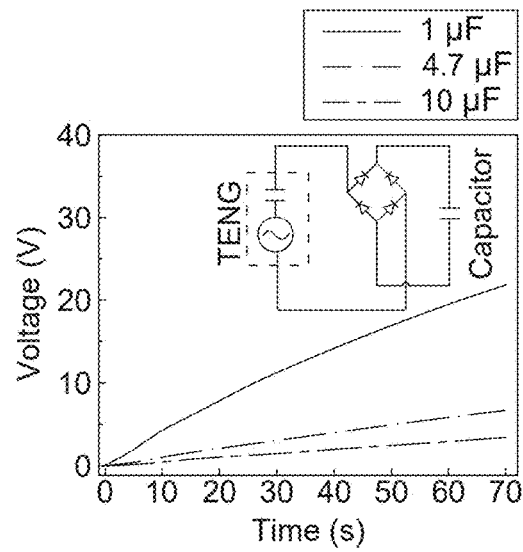
Figure 4F:
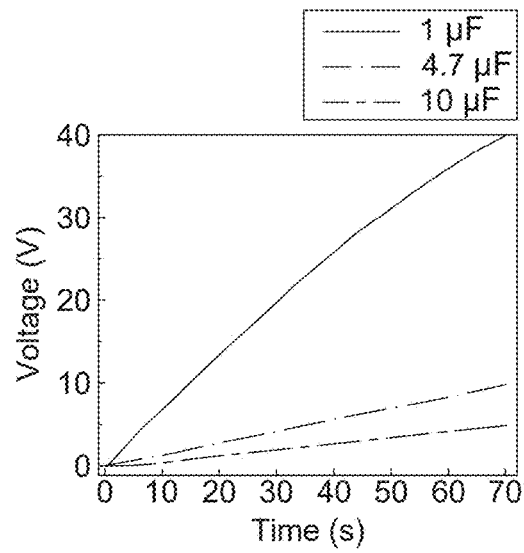

The power curve under different loads of this textile based TENG is depicted in FIG. 4b for hand tapping motion. As shown, an average of 460V peak-to-peak voltage can be generated through the hand tapping, and a peak output power of 2.67 mW is measured with a load resistance of 9 MΩ. This gives a power density of 166 uW/m$^3$. The energy generated from different body motions can thus be stored for further use. FIG. 4 shows the charging curve for commercial capacitors with varying capacitances of the textile based TENG. The charging curves of capacitors with capacitance of 1 μF, 4.7 μF, and 10 μF are illustrated in FIG. 4e for hand tapping and FIG. 4f for foot tapping. To a 1 μF capacitor, the charged voltage can reach up to 19V in around 60 s. And a capacitor with a capacitance of 10 μF can be charged up to 3V in around 60 s. When compared with hand tapping, the power generation performance of foot stepping is an enhancement.

Strain Sensor for Finger Bending Sensing and Robotics Control

Height-Varying Multi-Arch Strain Sensor

Where two or more arches are provided, each of said two or more arches may be of a different size (e.g. height) to at least one other of said two or more arches. In some embodiments, the arches may be on different portions or strips of textile. In other embodiments, there may be a single strip of the sensory textile with the two or more arches forming a series of arches along the strip.

Additionally, a multi-arch varying-height design could provide a wider sensing range from small strain to large strain. Results are shown in FIG. 5a for arch heights of 1 mm, 3 mm, 6 mm, 9 mm, and 12 mm respectively. Thus, the series of arches are of progressively larger size. The real time output of this multi-arch strain sensor under 30% strain, 100% strain, and 160% strain is depicted in FIG. 5e. Relevantly, FIG. 5 shows FIG. 5(a) a single-arch based strain sensor with different arch height under different strain conditions. The higher the arch the greater the ability to cope with elongation or strain, and the greater the maximum attainable triboelectric charge. FIG. 5(b) is a schematic diagram of multi-arc strain sensor under stretching. It shows the progressive flattening of arches under successively greater elongation of the substrate 218. The varying arch height enables detection of the amount of elongation or strain—the different arch heights result in different triboelectric charge values and thus a specific triboelectric charge is indicative of a specific elongation such that measuring the triboelectric charge may specifically determine the elongation or strain. FIG. 5(c) is a photo of as-fabricated sensor 220 with five, progressively higher arches. FIG. 5(d) is the modelled output voltage of the five arch sensor of FIG. 5(c), and FIG. 5(e) real time output of this multi-arch strain sensor 220 under 30% strain, 100% strain, and 160% strain. FIG. 5e shows a clear, direct correlation between the amount of elongation and the output voltage.

Figure 6A:
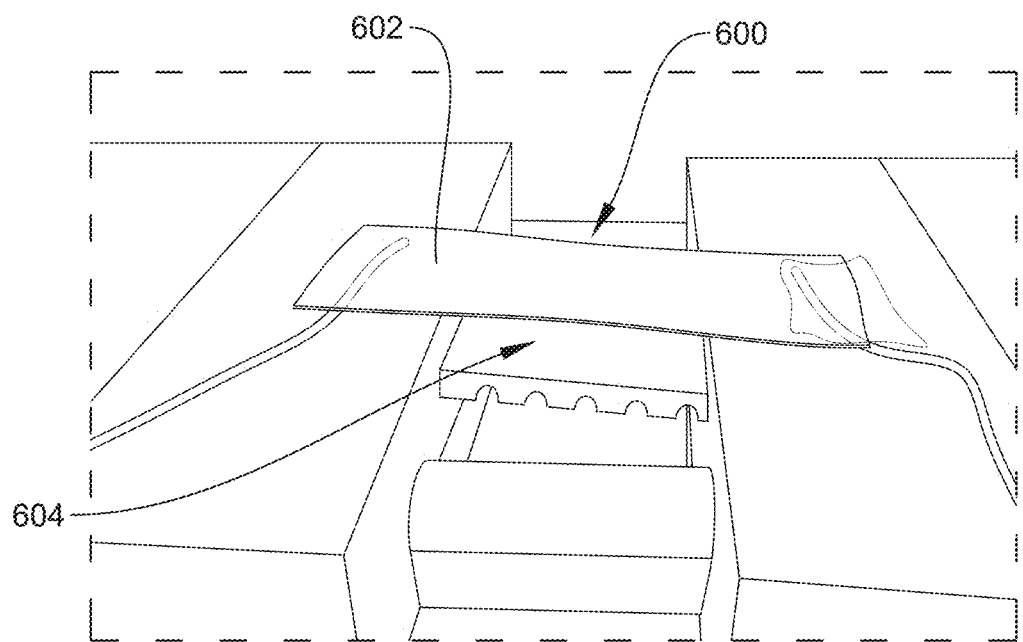
FIGS. 6a and 6b, illustrates.
Figure 6B:
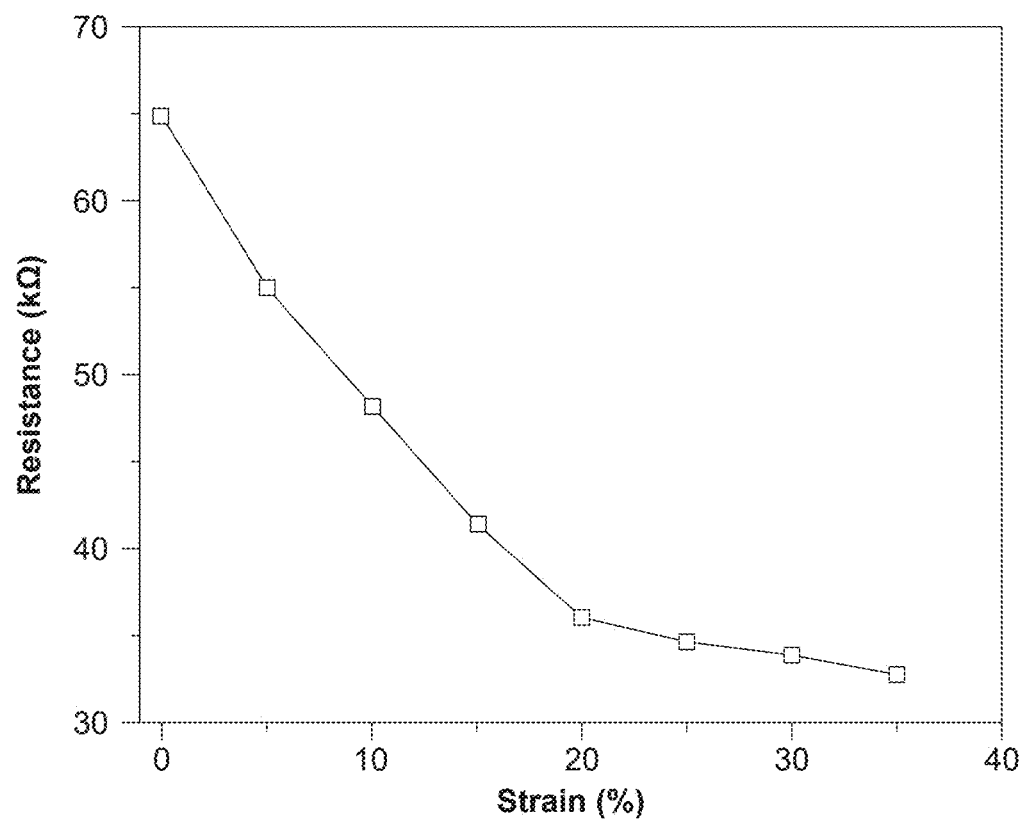

Resistance change characterization is a common sensing mechanism for most of the strain sensors, and a textile coated with conductive nanoparticles is also a potential configuration for strain sensing. A PEDOT:PSS coated textile strip with a width of 1 cm and a length of 2 cm was also tested. The resistance of the strip under different strain is measured and depicted in FIG. 6. Relevantly, FIG. 6 shows (a) a test setup of a resistive strain sensor, and (b) the relationship between resistance and strain. The strain sensor is a multi-arch strain sensor 600. The multi-arch strain sensor 600 is based on the PEDOT:PSS functionalized textile 602 as demonstrated in FIG. 5. Ecoflex, which is a highly stretchable and triboelectric negatively polymer, may be used for the bottom layer 604 to provide negative charges—other triboelectric negative materials may be substituted for the PTFE or Eco-flex materials as appropriate. This triboelectric strain sensor 600 works in the single-electrode mode. When there is no strain applied to the sensor 600, the PEDOT:PSS functionalized textile 602 will stay separated from the bottom Eco-flex thin film 604. When the arch is stretched, the textile 602 will be straightened and contact with the Eco-flex thin film 604 as shown—the device 600 being depicted in a 'use' or 'charge generation' condition—resulting in the generation of triboelectric charges on the contact surface—i.e. the surface at which the textile 602 touches the thin film 604—and the output will then depend on the stretching elongation, which is related to the strain.

A good linear response from 5% to 20% strain can be observed, but the largest strain that the device 600 can withstand is only 35% due to the limited elongation of the textile structure. For an applied strain of 20%, the relative resistance change of the textile strip is ΔR/R0=45%, where R and R0 are the resistance with and without applied strain and ΔR=|R-R0|.

Arch Shaped Finger Bending Sensor

Figure 7A:
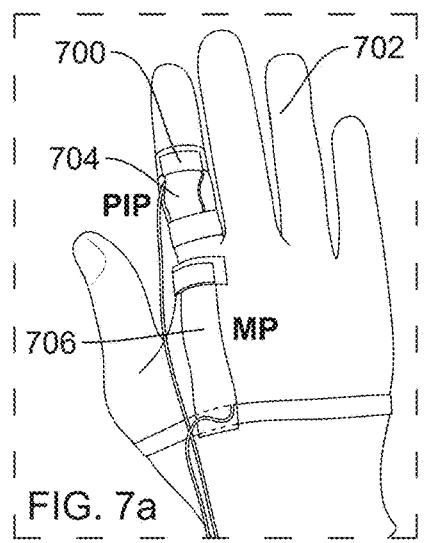
FIGS. 7a to 7c and 7e to 7k, illustrates.
Figure 7B:
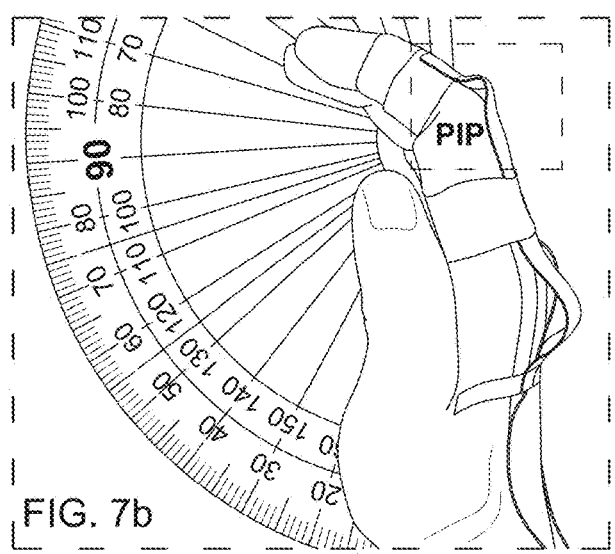
Figure 7E:
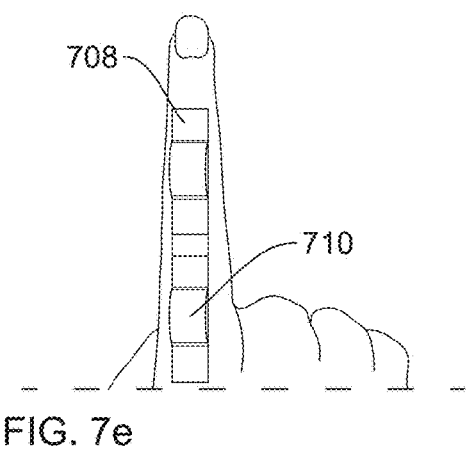
Figure 7F:
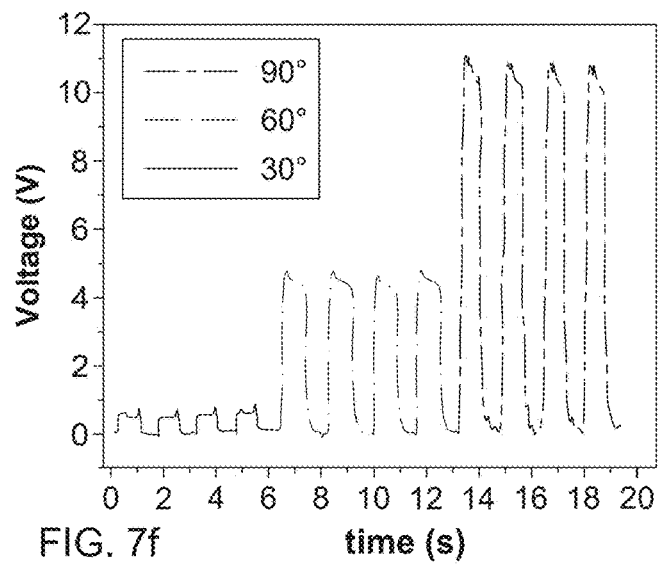
Figure 7I:
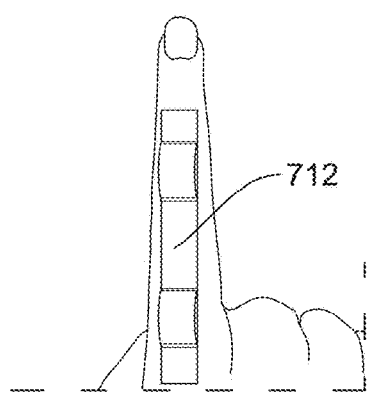
Figure 7J:
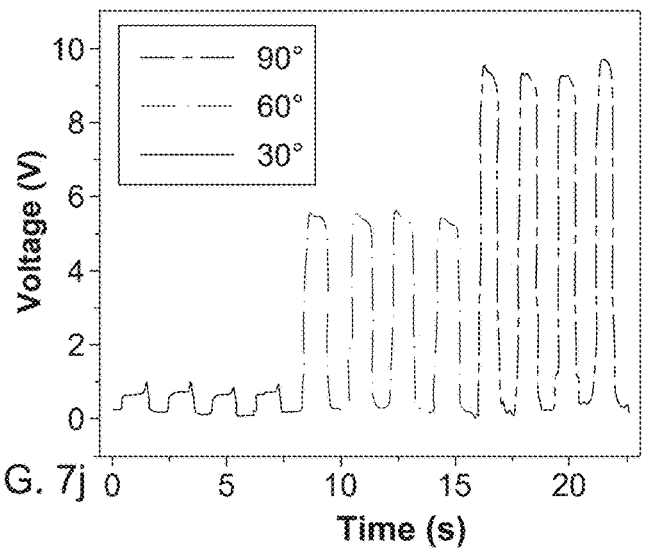
Figure 7C:
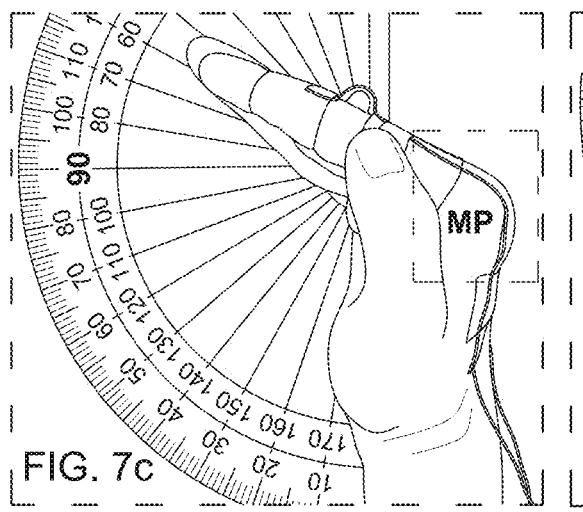
Figure 7D:
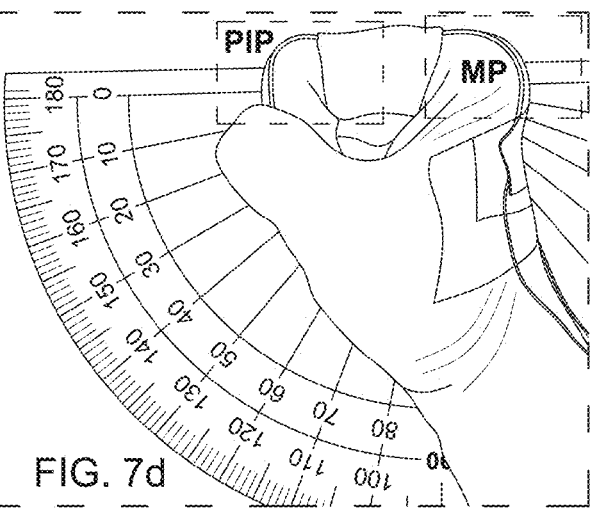
FIG. 7d—image of the sensor and hand of FIG. 7a, with the hand bent to activate both the first and second arches of the two-arch sensor.
Figure 7G:
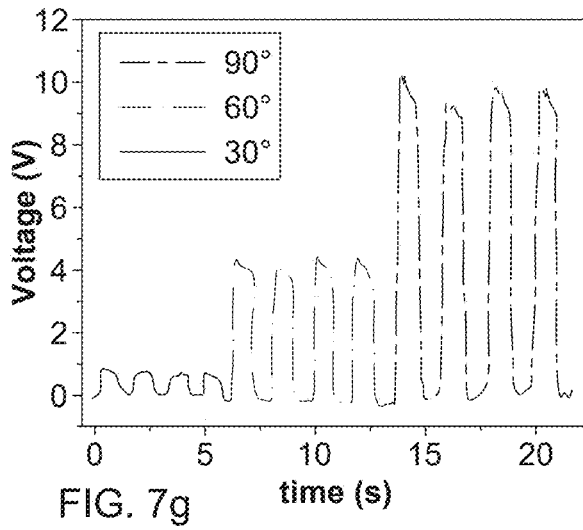
Figure 7H:
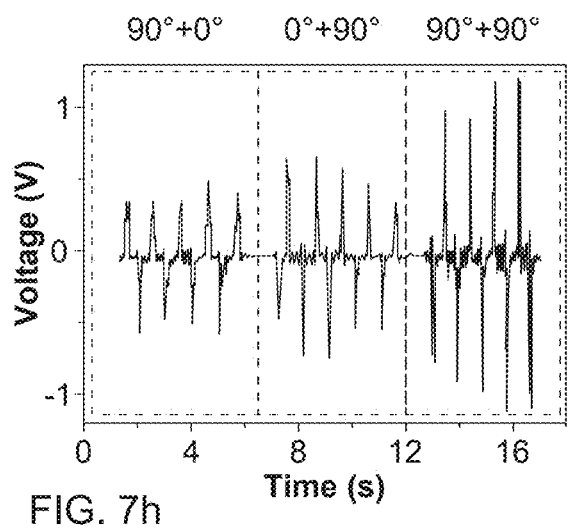
Figure 7K:
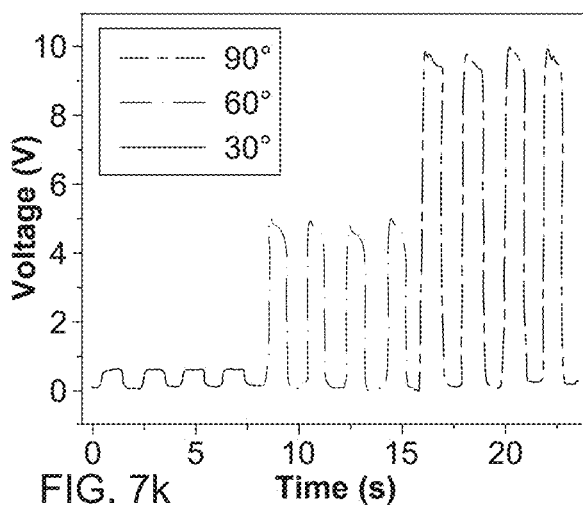
Figure 7L:
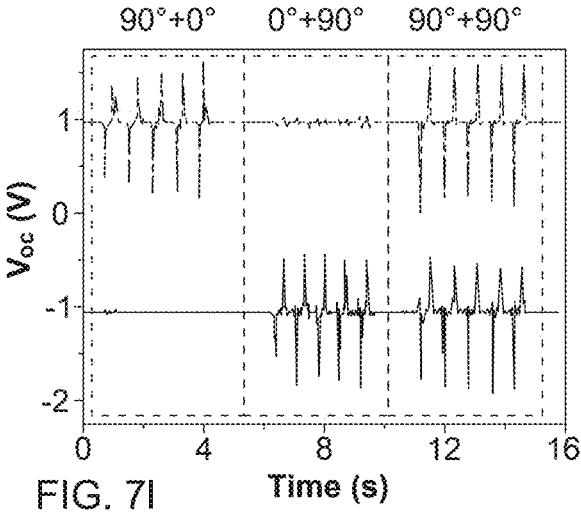

Similarly, a two-arch shaped strain sensor based on the PEDOT:PSS functionalized textile and Eco-flex thin film for finger motion detection is shown in FIG. 7(a). Relevantly, FIG. 7 shows FIG. 7(a) a photo of as-fabricated finger bending sensor 700 mounted to a user's hand by a glove 702 with an arch 704 over the proximal interphalangeal joint (PIP) and an arch 706 over the metacarpophalangeal joint (MP), where FIG. 7(b) provides, schematically, an embodiment with two separate arches 708, 710 and FIG. 7(f) shows both arches in a single, continuous textile strip 712. When a user bends a hand, a corresponding elongation of arch 704 bending results. A corresponding signal is shown in FIG. 7(c) for the two separate sensors design (i.e. FIG. 7(b)) and FIG. 7(g) for the single sensor design (i.e. FIG. 7(f)). When a user bends the MP bending, a corresponding signal is shown in FIG. 7(d) the two separate sensors design and FIG. 7(h) the single sensor design. Where both arches 704, 706 bend, the corresponding outputs for the two separate sensor design is observed in FIG. 7(e) and the single sensor design FIG. 7(i).

The finger bending sensor of FIG. 7(a) is attached onto the human index finger for characterization. Each arch sits right above one finger joint to sense the bending movement of the finger joint. The PIP and the MP of the index finger are indicated in the figures, and the output signal of PIP and MP corresponding to different bending angles are also shown.

Applications for Hand Motion Capture

To decouple the two parameters (PIP and MP), a new design of two arches is fabricated using two pieces of textile in non-contacting arrangement—i.e. no connection, such as direct connection, either physically or electrically. Each arch structure can readily identify the bending angles of the corresponding finger joint. Using the optimized finger bending sensor, applications can be demonstrated in hand motion capturing. By attaching the two-arch shaped finger bending sensors onto both the index and the middle finger as indicated by numerals 800 and 802 in FIG. 8a, the four hand motions which represent four alphabet signs "A", "B", "C", "D" in the American Sign Language with different bending angles of the index and middle fingers can be measured and achieved. Relevantly, FIG. 8 shows FIG. 8(a) a photo of as fabricated finger gesture sensor, comprising sensors 800 and 802, FIG. 8(b) illustrates the alphabet signs "A", "B", "C", "D" in American Sign Language, and output signals from the four electrodes (two per sensor 800, 802) and shown for "A" in FIG. 8(c), "B" in FIG. 8(d), "C" and FIG. 8(e) and "D" in FIG. 8(f). A single instance of performance of the hand gesture or sign is bounded by a broken-line box in each output figure.

Applications for Robotic Hand Control

The finger sensor also offers the possibility of providing a sensing signal for robotic hand control. The output signal from each sensor is recorded and processed to control the movement of the robotic hand, and the amplitude of the output determines the bending angles of the robot hand controlled through a computer. The output signals of each arch-shaped sensor is illustrated in FIG. 9. Relevantly, FIG. 9 shows the output signals corresponding from the four electrodes or sensory devices mounted to the hand.

Smart Textile for Healthcare Applications

Activity Monitoring

Detection and monitoring of human actions is useful in many applications such as patient monitoring. A wearable human motion detection platform based on the smart textile (e.g. a garment incorporating a sensory textile as described above) for healthcare monitoring is developed as shown in FIGS. 10a to 10d. Relevantly, FIG. 10 shows photos of activity monitoring sensors on the hip as shown in FIG. 10(a), the arm as shown in FIG. 10(b), the elbow as shown in FIG. 10(c), and the knee as shown in FIG. 10(d). FIG. 10(e) shows the output signals of the four sensors shown in FIGS. 10(a) to 10(d) under various scenarios—e.g. standing up (1000), walking (slow 1002a, fast 1002b), running (1004), exercises (slow 1006a, fast 1006b), falling down (1008), and sitting down (1010).

The whole system contains four parts to differentiate different human motions. A simple three-layer structured TENG based on the smart textile described above is fabricated and attached onto an arched polyethylene terephthalate (PET) thin film as demonstrated in FIG. 10. A self-powered sensor is put onto the hip as shown in FIG. 10(a) to detect the sitting-down or standing-up motion and attached right beneath the knee as shown in FIG. 10(d) to sense a sudden fall-down. A multi-arch shaped strain sensor is placed onto the elbow as shown in FIG. 10(c) to record the movement of the human arm, and together with a textile based TENG attached on sleeve and underneath the arm separately as shown in FIG. 10(b), the human activities can be more precisely differentiated. A sensory textile device may, for example, include a sensory textile configured to be positioned at a first location on a human body, and a spacer layer and conductive backing configured to be positioned at a second location on the human body that moves past the first location as shown in FIG. 10(b) during a movement of the human body, thereby to activate the sensory textile device. This activation may be through triboelectric properties of the sensory device.

Through monitoring of the bending angle and the moving speed of the arm, useful information can be collected of the exercise performed by the human body. If the person goes through a sudden falling incident when walking or running, an enormous large positive peak voltage can be detected from the device as shown at 1008. This could be used for fall detection for the elderly or the disabled. A wireless transmitting module could be implemented to set up an alarm to inform a hospital if the person did not stand up after a short period from a detected fall. A negative output voltage can only be detected when the person stands up from the ground.

$CO_2$ Sensing

Figure 11A:
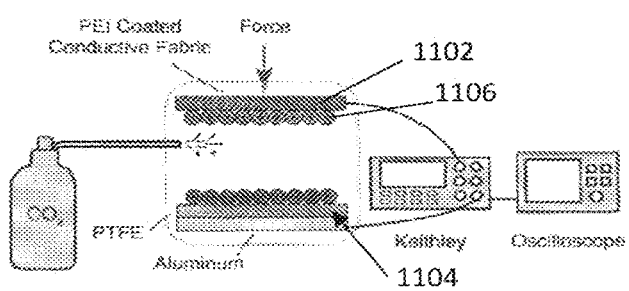
FIGS. 11a and 11b, illustrates.
Figure 11B:
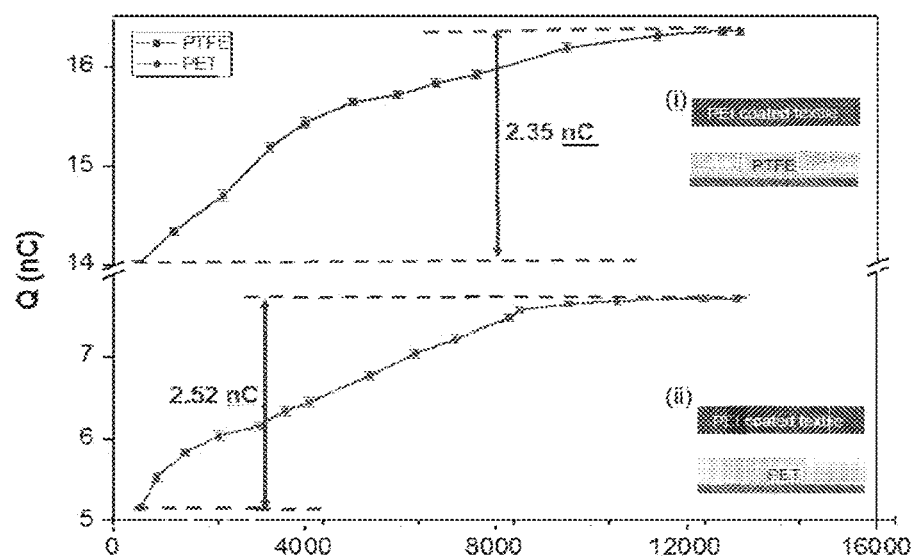

To demonstrate the application of the textile based TENG as a CO2 sensor, polyethylenimine (PEI) solution was spray coated onto the PEDOT:PSS functionalized textile surface. The cotton fabric is coated with non-diluted PEDOT:PSS solution in this section to achieve a better conductivity. The PEI gel was diluted 10-fold with DI water for spray coating. To perform the contact-release cycle, the frequency of the moving stage is set as 0.5 Hz and the force is set as 10N. With the absorption of CO2 after spray or injection between the sensory textile 1102 and substrate 1104 as shown in the schematic diagram of the test setup of PEI coated $CO_2$ sensing textile in FIG. 11(a), a carbamate layer 1106 which is a CO2-PEI complexation will be formed and in turn change the electronegativity of the PEI layer 1102. This electronegativity change can be projected on the transferred charges of the triboelectric nanogenerator. The transferred charge or charge responses on the sensor over varying $CO_2$ concentration of the textile based TENG with triboelectric negative material of PTFE and PET (contact layer) is depicted in FIG. 11b.

The transferred charge Q increases with $CO_2$ concentration and the Q almost saturates when the $CO_2$ concentration reaches 10000 ppm for both devices. For the TENG with PTFE as negative triboelectric material, the transferred charge increases from 5.35 nC to 7.67 nC where it reaches its saturation, with a sensitivity of 2.69×10−4 nC/ppm.

PEDOT:PSS Coated Smart Socks

Smart Socks as Triboelectric Energy Harvester With Piezoelectric Force Sensor

Figure 12B:
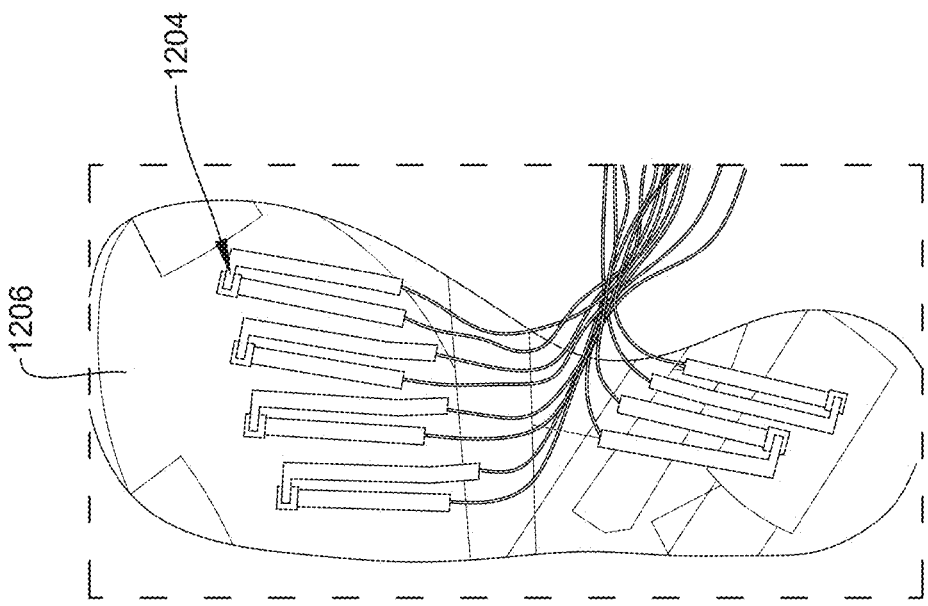
FIGS. 12a to 12c, illustrates.
Figure 12A:
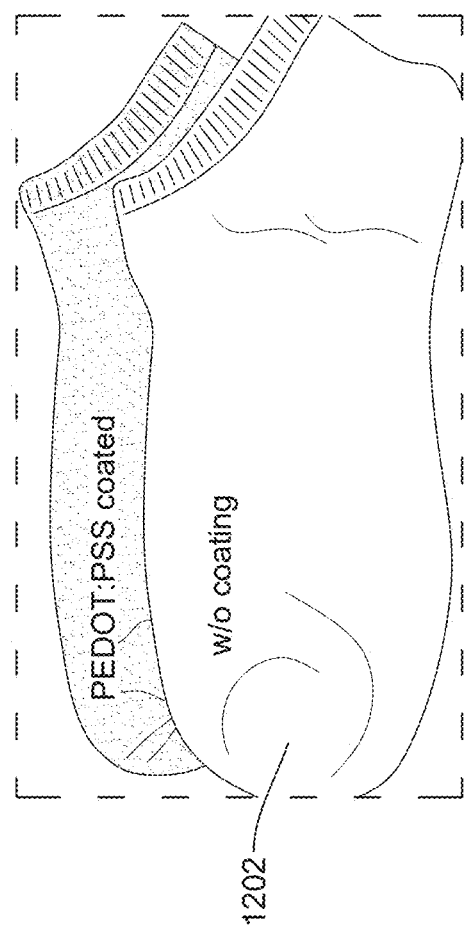
Figure 12C:
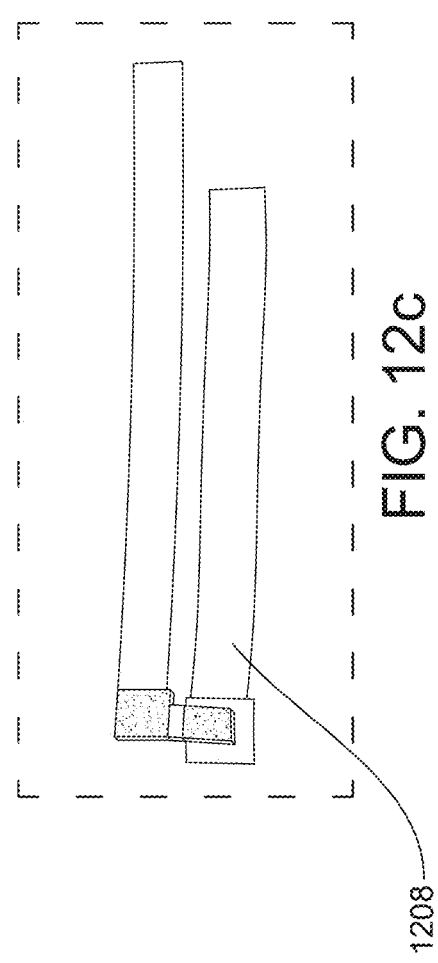
Figure 13A:
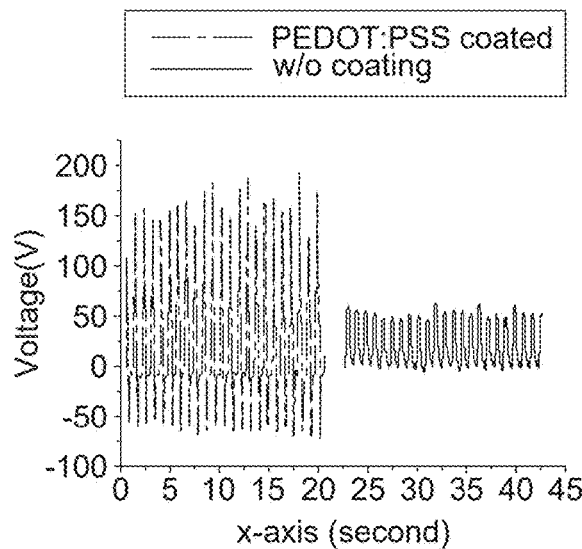
FIGS. 13a to 13d, illustrates.
Figure 13B:
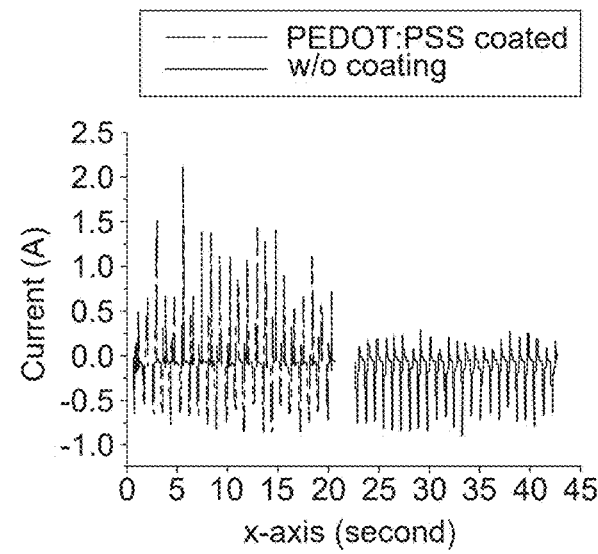
Figure 13C:
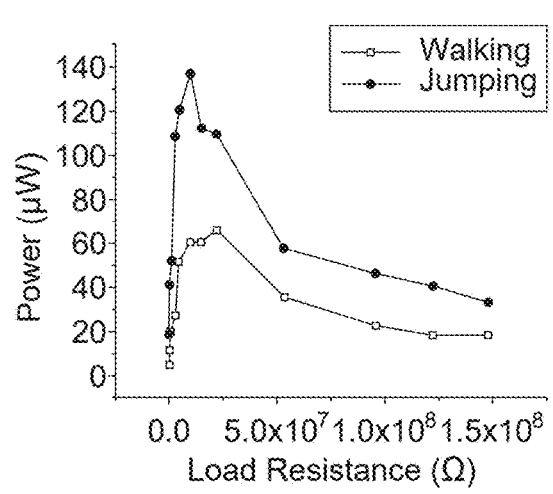
Figure 13D:
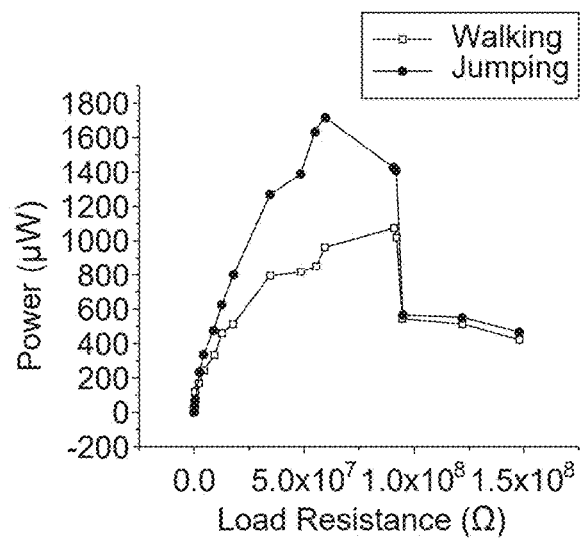

Mechanical energy from the motion of foot is considered a significant power source that can be converted into electricity through the triboelectric effect. Previous studies have mainly focused on insole energy harvesters. PEDOT:PSS coated smart socks are able to make the textile itself into an effective triboelectric material due to the conductivity of the coating. Hence, as shown in FIG. 12(a), socks have been designed in accordance with present teachings to generate power while being more compact and comfortable for wearing than a generator incorporated directly into the sole of the shoe. FIG. 12(a) shows PEDOT:PSS coated socks 1200 and the original socks 1202. FIG. 12(b) shows the as-fabricated PZT sensor arrays 1204 on PDMS substrate 1206 (before being embedded into socks), and FIG. 12(c) is a close-up of a single PZT sensor unit 1208 with top and bottom electrode.

FIG. 13 shows the measured output power under difference scenarios. Within shoes, each sock can provide the maximum power of 137 W and 66 W for jumping/running and walking, respectively. Without shoes, as the space of complete triboelectric contact/release cycle increases, the output power can be further boosted up to 1.7 mW and 1.1 mW. PTFE film is used as negative contact material during the test. As shown in FIGS. 12b and 12c, to achieve a real smart socks, lead zirconate titanate (PZT) chips are thinned down to 50 um to make a flexible force sensor which is small enough to be embedded into socks without losing the comfortability. FIG. 13 shows a comparison of output voltage and (b) current between PEDOT:PSS coated socks and non-coated socks—FIGS. 13(a) and 13(b) respectively. FIG. 12(c) shows the power curve of smart socks within the shoes, under walking and jumping conditions. Similarly, FIG. 13(d) shows the power curve of smart socks without shoes and while under walking and jumping conditions.

Smart Socks as Motion, Gait, and Force Sensor

Figures 14A, 14B:
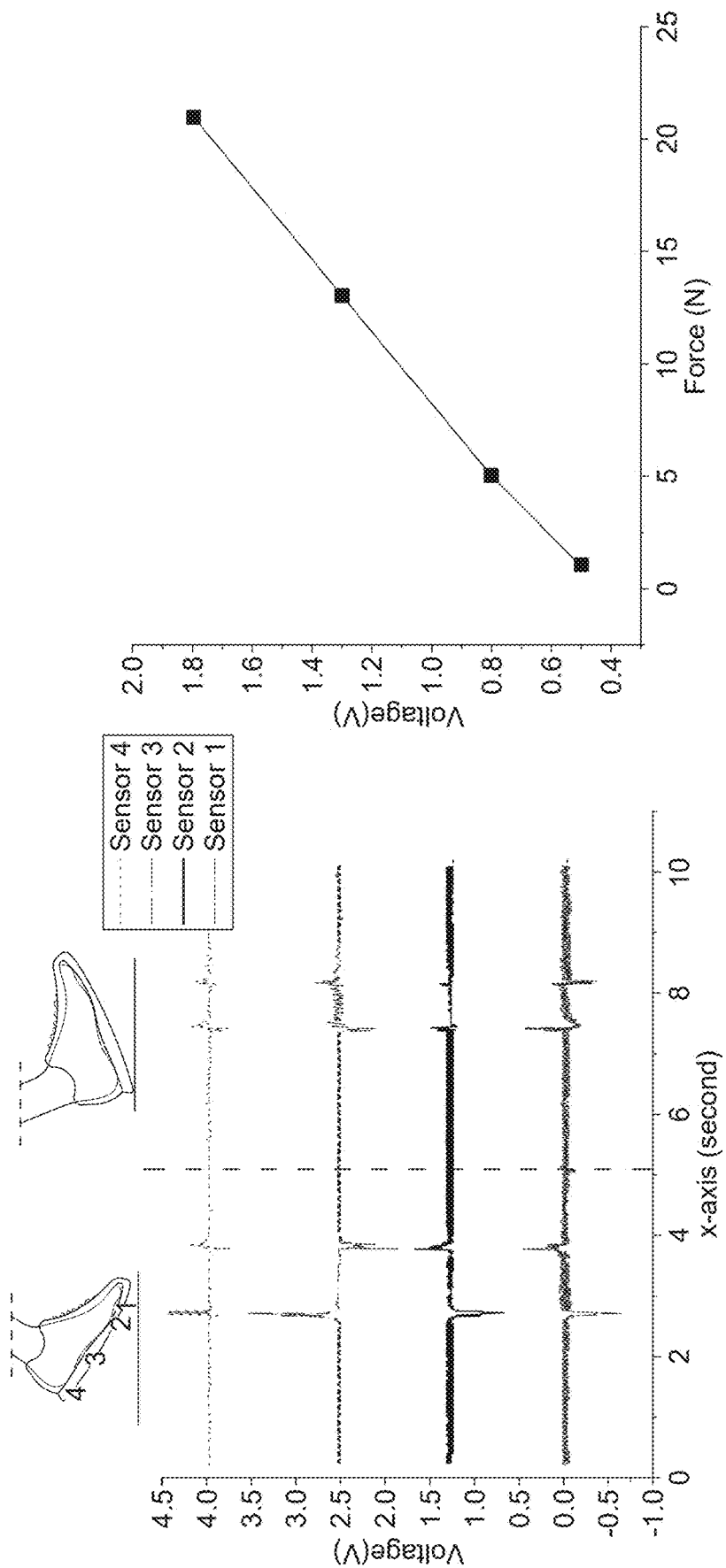
FIGS. 14a to 14c, illustrates.
Figure 14C:
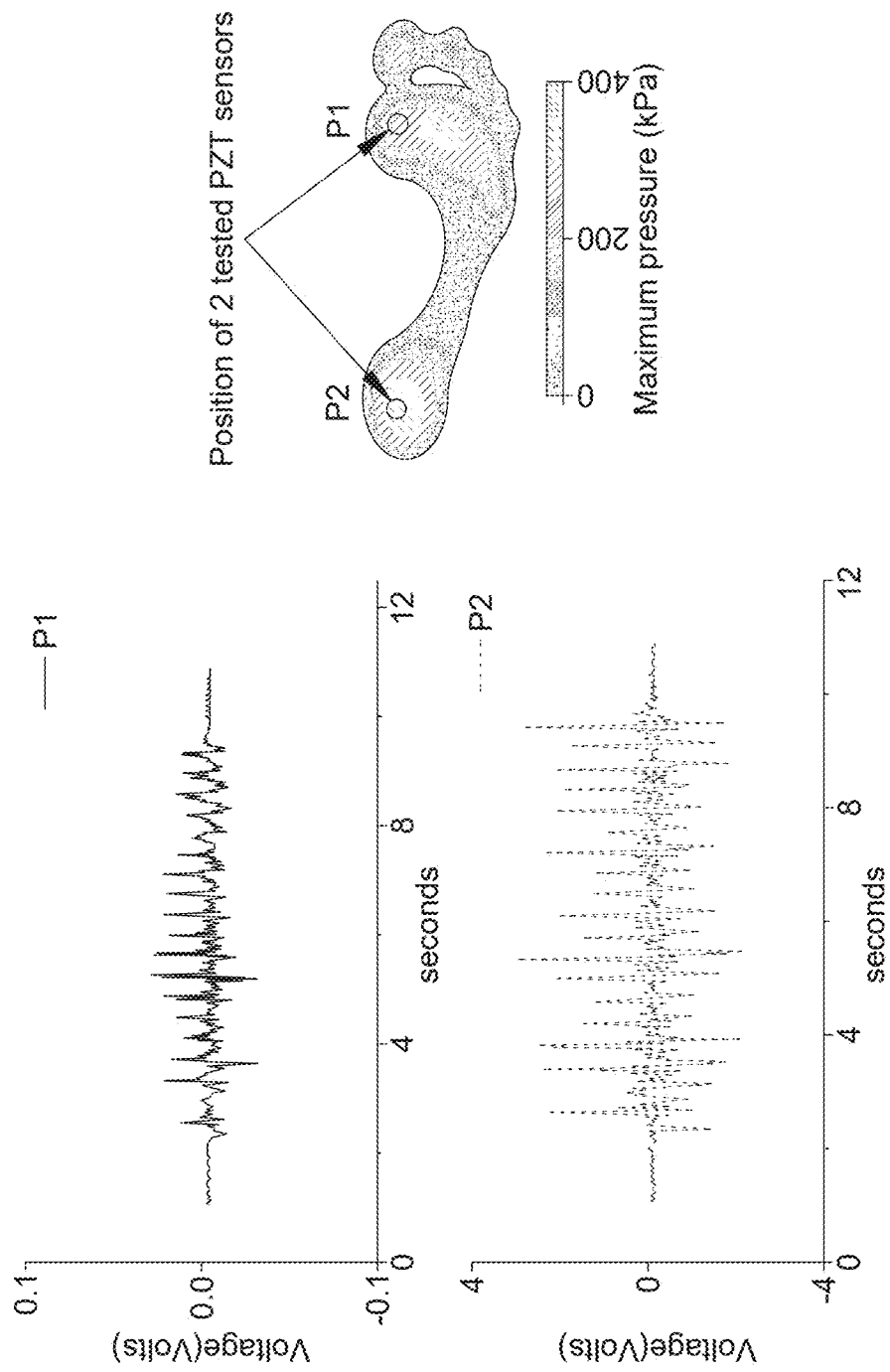

Based on the working principle of the triboelectric effect, the physical sensor can also be realized by integrating multiple electrodes into socks or shoes. In FIG. 14, by designing a PTFE insole with four electrodes, gait and the position can be identified with larger pressure through the signal peaks. In addition, as shown in FIG. 14c, the embedded thin PZT force sensor can provide more quantitative pressure analysis from movements, due to its high sensitivity. Relevantly, FIG. 14 shows, for a triboelectric sensor: FIG. 14(a) gait monitoring by multiple electrodes, toe and heel contact, FIG. 14(b) output voltage vs. force calibration, and for PZT piezoelectric force sensors: and FIG. 14(c) output signals from 2 corresponding positions during walking, compare to theoretical foot pressure mapping.

Smart Socks as Sweat Sensor

Figure 15:
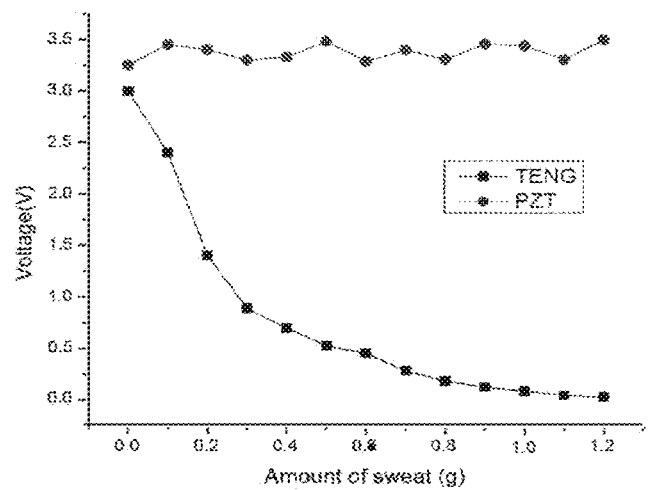
FIG. 15 shows the open circuit output voltage of a PZT sensor and triboelectric sensor in a sock under increasing sweat conditions.

Triboelectric performance is related to humidity, in terms of output. To utilize this feature, a sweat sensor is developed together with piezoelectric sensors. More specifically, both contact force and humidity can affect the triboelectric power generation. To eliminate the influence of force fluctuation, the PZT force sensor will act as a baseline, since it will not vary with humidity. Therefore, as shown in FIG. 15, by measuring the triboelectric and piezoelectric signals simultaneously, we can obtain a rough data about the sweat status of foot, for further sports monitoring or healthcare use. Relevantly, FIG. 15 shows the output voltage of the PZT sensor and triboelectric sensor in either separate, closely positioned devices, or in the same device (e.g. a garment such as a sock) under increasing sweat conditions. 0.9 wt % of NaCl solution is used to mimic sweat.

The first generation of such smart textiles only used the textile as a substrate that was integrated with rigid and miniaturized electronic components. Intrinsically flexible and wearable sensors based on textile or fabric have emerged, to realize a seamless integration of multi-function sensors and textiles. The common sensing mechanism of the textile-based flexible or stretchable sensors is based on the resistance change which still cannot bypass the essential issue of power consumption. To solve this matter, fabric based TENG has emerged for energy harvesting and self-powered sensing due to the unique advantages of being soft, light-weight, air permeable, having a natural micro-structure, and due to the low-cost of the textile. However, the further advancement of the textile-based and self-powered sensors of the prior art still faces challenges making its way to large scale production for practical use.

In accordance with the present disclosure, a PEDOT:PSS functionalized smart textile for diversified wearable applications is fabricated with a facile and low-cost process. Large-scale energy harvesting, physiological sensing, as well as chemical sensing properties can be realized with more compact and comfortable solutions. The generated power can be stored to support the operation of other wearable devices.

The possible industrial applications of the methods and devices disclosed herein include textile based multi-mode energy harvesters, self-powered strain sensors, gesture sensors, motion sensors, chemical sensors with different enzyme coatings, sweat sensors, force sensors for healthcare, virtual reality, smart control, and entertainment applications.

During testing, PEDOT:PSS coatings may show some degradation after washing if there is no specific treatment given. But it is possible solve or reduce this issue by consulting surface treatment techniques that are available from textile industries to prevent the coated PEDOT:PSS molecules being washed away when the clothes or textiles are washed in a washing machine.

The present teachings may be used to produce a garment comprising a sensory textile device as described herein.

Many modifications will be apparent to those skilled in the art without departing from the scope of the present invention.

Throughout this specification, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference to any prior art in this specification is not, and should not be taken as, an acknowledgment or any form of suggestion that the prior art forms part of the common general knowledge in Australia and elsewhere.

The invention claimed is:

1. A method for forming a sensory textile, comprising:
providing a conductive polymer, a dopant and a solvent;
mixing the conductive polymer, dopant and solvent to form a mixture having a predetermined ratio of the conductive polymer and the dopant, and a predetermined concentration of the conductive polymer;
contacting a fabric with the mixture to coat the fabric with the conductive polymer and dopant; and
drying the coated fabric,
wherein the sensory textile is used to generate a charge.

2. A method according to claim 1, wherein providing a conductive polymer comprises providing a conductive organic polymer.

3. A method according to claim 1, wherein the conductive polymer is provided as a dispersion in a solution.

4. A method according to claim 1, wherein providing a conductive polymer comprises providing poly (3,4-ethylenedioxythiophene): poly (styrene sulfonate) (PEDOT:PSS).

5. A method according to claim 1, wherein providing a dopant comprises providing a dopant to improve the conductivity of the conductive polymer once dried on the coated fabric.

6. A method according to claim 5, wherein providing a dopant comprises providing dimethyl sulphoxide (DMSO).

7. A method according to claim 1, wherein mixing the conductive polymer, dopant and solvent to form a mixture having a predetermined ratio of the conductive polymer to dopant, comprises doping the conductive polymer with 5 wt % of the dopant.

8. A method according to claim 1, wherein providing a solvent comprises providing water.

9. A method according to claim 8, wherein providing water comprises providing eeionized water.

10. A method according to claim 1, wherein mixing the conductive polymer, dopant and solvent to form a mixture having a predetermined concentration of the conductive polymer, comprises mixing the conductive polymer, dopant and solvent to form a mixture having 12.5% conductive polymer.

11. A method according to claim 1, wherein drying the coated fabric comprises drying the coated fabric for at least 30 minutes at 80° C.

12. A sensory textile device comprising:
a sensory textile comprising a fabric coated in a conductive polymer and dopant at a predetermined ratio; and
a substrate,
wherein the sensory textile is attached to the substrate at at least two spaced apart locations and has a rest condition, in which the sensory textile is spaced from the substrate between the at least two spaced apart locations, and a generating condition, in which the sensory textile is in contact with the substrate between the at least two spaced apart locations, wherein moving from the rest condition to the generating condition causes a charge to be generated.

13. A sensory textile device according to claim 12, wherein the sensory textile forms an arch between the at least two spaced apart locations, and stretching the substrate brings the sensory textile into the generating condition.

14. A sensory textile device according to claim 13, wherein the sensory textile forms two or more arches, the two or more arches being attached to the substrate between respective pairs of locations of said at least two spaced apart locations.

15. A sensory textile device according to claim 14, wherein the sensory textile comprises at least two sensory textile portions attached to the substrate in a non-contacting arrangement.

16. A sensory textile device according to claim 12, being configured to be worn on a finger, the spaced apart locations being on opposite sides of a knuckle of the finger.

17. A sensory textile device according to claim 14, being configured to be worn on a finger, the pairs of locations of one of said two or more arches being located on opposite sides of a knuckle of the finger and the pairs of locations of a different one of said two or more arches being located on opposite sides of a different knuckle of the finger.

18. A sensory textile device according to claim 14, wherein each of said two or more arches is of a different size to at least one other of said two or more arches.

19. A sensory textile device according to claim 18, comprising a single strip of the sensory textile, and said two or more arches form a series of arches along the strip.

20. A sensory textile device according to claim 19, wherein the series of arches are of progressively larger size.

21. A sensory textile device according claim 12, wherein the sensory textile is formed by the method of claim 1.

22. A sensory textile device comprising:
a sensory textile formed according to claim 1;
a conductive backing layer; and
a spacer layer disposed between the sensory textile and conductive backing layer.

23. A sensory textile device according to claim 22, wherein the spacer layer is polytetrafluoroethylene (PTFE).

24. A sensory textile device according to claim 22, wherein the conductive backing layer is Aluminium.

25. A sensory textile device according to claim 22, wherein the sensory textile is configured to be positioned at a first location on a human body, and the spacer layer and conductive backing are configured to be positioned at a second location on the human body that moves past the first location during a movement of the human body, thereby to activate the sensory textile device.

26. A garment comprising a sensory textile device according to claim 12.

27. The garment according to claim 26, wherein the garment is a sock for sensing a gait of a user.

* * * * *